(12) United States Patent
Abe et al.

(10) Patent No.: US 7,879,059 B2
(45) Date of Patent: *Feb. 1, 2011

(54) LANCET ASSEMBLY

(75) Inventors: Teruyuki Abe, Tokyo (JP); Kazuharu Seki, Tokyo (JP)

(73) Assignee: Izumi-Cosmo Company, Limited, Osaka (JP)

( * ) Notice: Subject to any disclaimer, the term of this patent is extended or adjusted under 35 U.S.C. 154(b) by 166 days.

This patent is subject to a terminal disclaimer.

(21) Appl. No.: 11/664,821

(22) PCT Filed: May 17, 2005

(86) PCT No.: PCT/JP2005/008960

§ 371 (c)(1),
(2), (4) Date: Apr. 6, 2007

(87) PCT Pub. No.: WO2006/038340

PCT Pub. Date: Apr. 13, 2006

(65) Prior Publication Data

US 2008/0058847 A1 Mar. 6, 2008

(30) Foreign Application Priority Data

Oct. 6, 2004 (JP) ............................. 2004-293904

(51) Int. Cl.
*A61B 17/32* (2006.01)
(52) U.S. Cl. ...................................... 606/182; 606/181
(58) Field of Classification Search ................ 606/181, 606/182; 604/136, 110, 111, 192, 195; 600/580; 83/397–398; 401/134; 220/212, 810, 254.1, 220/200; 222/52, 526, 83, 83.5; 206/363, 206/364, 365
See application file for complete search history.

(56) References Cited

U.S. PATENT DOCUMENTS 4,442,836 A * 4/1984 Meinecke et al. ............ 606/182
4,677,979 A * 7/1987 Burns ......................... 606/172

(Continued)

FOREIGN PATENT DOCUMENTS

| JP | 2002-143132 | 5/2002 |
| JP | 2003-153885 | 5/2003 |
| WO | 96/16599 | 6/1996 |
| WO | 03/070099 | 8/2003 |
| WO | 03/071940 | 9/2003 |

OTHER PUBLICATIONS

Japanese Office Action issued Sep. 7, 2010 in corresponding Japanese Application No. 2006-539153.

*Primary Examiner*—(Jackie) Tan-Uyen T Ho
*Assistant Examiner*—David Eastwood
(74) *Attorney, Agent, or Firm*—Wenderoth, Lind & Ponack, L.L.P.

(57) ABSTRACT

A lancet assembly is disclosed which eliminates the need for removing a resin cover that covers a pricking element. When a lancet structure is inserted into a lancet holder, a force is applied so as to separate a lancet cover, that encloses a distal end of a pricking element, from a lancet body so that the distal end of the pricking element which has been enclosed by the lancet cover is exposed in the lancet holder, and the opening of the lancet holder is positioned in front of the distal end of the pricking element. The lancet structure has a trigger which launches the pricking element of which the distal end is exposed, when the lancet structure is continually pushed into the lancet holder.

26 Claims, 18 Drawing Sheets

U.S. PATENT DOCUMENTS

| | | | |
|---|---|---|---|
| 4,869,249 A * | 9/1989 | Crossman et al. | 606/182 |
| 5,439,473 A * | 8/1995 | Jorgensen | 606/182 |
| 5,628,765 A * | 5/1997 | Morita | 606/182 |
| 5,755,733 A * | 5/1998 | Morita | 606/182 |
| 6,358,265 B1 * | 3/2002 | Thorne et al. | 606/181 |
| 6,616,616 B2 | 9/2003 | Fritz et al. | |
| 7,150,755 B2 | 12/2006 | LeVaughn et al. | |
| 2003/0050573 A1 | 3/2003 | Kuhr et al. | |
| 2004/0092997 A1 * | 5/2004 | Levin et al. | 606/181 |
| 2004/0243164 A1 * | 12/2004 | D'Agostino | 606/181 |
| 2005/0015020 A1 | 1/2005 | LeVaughn et al. | |
| 2005/0021066 A1 | 1/2005 | Kuhr et al. | |
| 2006/0178600 A1 | 8/2006 | Kennedy et al. | |
| 2007/0088377 A1 | 4/2007 | LeVaughn et al. | |
| 2007/0225742 A1 * | 9/2007 | Abe et al. | 606/182 |

* cited by examiner

LANCET ASSEMBLY

TECHNICAL FIELD

The present invention relates to a pricking device or lancet assembly such as a finger pricking device used to take a small amount of blood as a sample by pricking the skin of a human body and, more particularly, to a lancet assembly of a disposable type which is easy to use.

BACKGROUND ART

Various finger pricking devices or lancet assemblies have been commercialized for use by consumers, as well as for the use in hospitals, clinics and private practitioners, in order to take a small amount of blood as a sample. Such a device includes a lancet which has an element having a sharp part, namely a pricking element (such as a needle-like element), that is used to quickly prick the skin of a patient, or penetrate the skin and form an incision opening so as to allow a small amount of blood to bleed.

Such a lancet assembly is sterilized beforehand as to its distal end portion in its manufacturing process, because the pricking element forms the incision opening. The assembly must be protected from contamination by the ambient environment so as to maintain the sterilized condition until the assembly is put into use. It is also necessary to keep the pricking element from being exposed unnecessarily, lest the pricking element causes injury to human or object nearby when it is being handled.

With such considerations described above, a lancet assembly has been proposed which comprises a lancet structure wherein a distal end of the pricking element is sealed with a resin, and also a lancet holder has been proposed which is to be used in combination with the lancet structure (see International Patent Publication WO96/16599).

To use the lancet assembly described above, it is necessary to remove a resin cover, which seals the distal end of the pricking element, from the lancet structure inserted in the lancet holder, then hold the lancet holder while pressing, for example, a finger tip onto an opening positioned at a front end of the lancet holder, and apply a force toward the finger tip so as to push the lancet structure into the lancet holder, thereby to launch a lancet of the lancet structure.

It is inconvenient to hold the lancet assembly with fingers of one hand and remove the resin cover which seals the distal end of the pricking element with fingers of the other hand, for using the lancet assembly. It is desired to eliminate such action to remove the cover.

When the lancet is launched by using the lancet assembly described above, the user may be forced to have a period of mental preparation for the anticipation of experiencing a pain caused by a needle-like pricking element which penetrates the skin, the period lasting from the completion of preparation for launching the lancet to the time when the lancet is launched, thus causing nervousness depending on the user. It is desired to relieve such nervousness.

SUMMERY OF THE INVENTION

Accordingly, an object of the present invention is to provide a novel lancet assembly capable of solving the problems of the conventional lancet assembly described above, in particular, a lancet assembly which does not require removal of its resin cover and which can relieve the nervousness which occurs before launching the lancet.

Through intensive studies for achieving the object described above, the inventors of the present application have reached a finding that the object described above can be achieved by a lancet assembly having such a constitution that when inserting a lancet structure into a lancet holder, a lancet cover is automatically removed from a pricking element so as to expose a distal end (or a tip portion) of the pricking element, by applying a force which separates the lancet cover, that surrounds the distal end of the pricking (or puncture) element, and a lancet body from each other. It has also been found that the nervousness can be relieved by such a constitution that the lancet of which distal end is exposed is automatically launched by inserting the lancet structure into the lancet holder, and then pushing the lancet structure into the lancet holder so as to expose the distal end of the pricking element and further continuing the pushing action.

The present invention, in the first aspect thereof, provides a lancet assembly comprising a lancet structure and a lancet holder which holds the lancet structure, wherein the lancet structure is constituted from an ejector and a lancet;

the ejector comprises a trigger, an arm, a spring and a base to which the trigger, the arm and the spring are attached, and the spring has a connector provided on a front end thereof and is connected to the base at a rear end thereof;

the lancet comprises a lancet body, a lancet cover and a pricking element which is present within the lancet body and the lancet cover while straddling across them, and a distal end of the pricking element is enclosed by the lancet cover;

the lancet body is connected to the connector;

the lancet holder has, at a front end thereof, an opening through which the distal end of the pricking element passes; and when the lancet structure is inserted into the lancet holder and the base is moved toward the connector, the arm applies a force to the lancet cover and the lancet body so as to separate them from each other while compressing the spring with the connector being engaged with the lancet holder, so that the lancet cover is separated from the pricking element and the distal end of the pricking element which has been enclosed is exposed, and when keeping the base further moving thereafter, the trigger disengages the engaged connector. The rear end of the spring may be attached, instead of or in addition to "to the base", preferably to a rear end of the arm or to the vicinity thereof, and more preferably to a foot of the arm where the arm is attached to the base or to the vicinity of such foot. Also a rear end of the trigger may be attached, instead of or in addition to "to the base", to the rear end of the arm or to the vicinity thereof, and more preferably to a foot of the arm where the arm is attached to the base or to the vicinity of such foot.

When the assembly having such a constitution as described above is used to take a blood sample, the lancet body is moved by pressing the base of the lancet structure which has been inserted into the lancet holder, then the connector, and therefore the lancet body is locked or engaged by the lancet holder so as to temporarily be disabled to further move further, and the distal end of the pricking element which has been enclosed by the lancet cover is exposed within the lancet holder, so that the opening of the lancet holder is disposed directly in front of the distal end of the pricking element (that is, the lancet cover does not lie on a trajectory of the lancet body having the exposed pricking element which trajectory is formed upon the pricking operation (the term "directly" is used in this sense), and thereby enabling it to prick without impeding the movement of the lancet body). That is, the distal end of the pricking element which has been enclosed by the lancet cover is automatically exposed. Then, when continuing to press the base, the trigger of the ejector unlocks the engagement of the lancet body, so that the lancet having the pricking element of which distal end is exposed is launched.

Locking of the lancet body, exposing the distal end of the pricking element and subsequently unlocking such locking by the trigger can be carried out successively (in the above mentioned order) by pressing the base continuously (namely, successively) into the lancet holder. Thus the lancet is automatically launched when the base is pressed into. That is, such a situation can be achieved wherein the lancet has been launched while the user thereof is unaware of it. It is of course possible that the above mentioned steps may also be intentionally carried out intermittently.

In one embodiment of the lancet assembly according to the present invention, the lancet cover is located in front of the arm;

the lancet cover and the lancet body are connected into an integral piece by a weakened portion; and the connector is bonded or connected to the lancet body; so that, when the base is moved relatively toward the connector (that is, they approach to each other) so as to compress the spring while keeping the front end of the arm in contact with a rear side of the lancet cover, the lancet cover and the lancet body are separated at the weakened portion. After separating in this way, when the lancet cover is moved away from the lancet body, the distal end of the pricking element is exposed which has been enclosed by the lancet cover.

In another embodiment the lancet assembly according to the present invention, the lancet cover is positioned in front of the arm;

the lancet cover and the lancet body are disposed independently from each other and are connected into an integral piece via the pricking element;

the connector is connected to the lancet body; so that, when the base is moved relatively toward the connector (that is, they approach to each other) so as to compress the spring while keeping the front end of the arm in contact with a rear side of the lancet cover, the lancet cover moves away from the lancet body. Thereafter, when the lancet cover is moved further away from the lancet body, and therefore from the pricking element, the distal end of the pricking element is exposed which has been enclosed by the lancet cover.

When the arm is moved forward while the distal end of the pricking element is exposed as mentioned above, the lancet cover which is separated from the lancet body and is in contact with the front end of the arm moves obliquely forward (for example, obliquely upward forward or obliquely downward forward), so that the opening positioned at the front end of the lancet holder is located directly in front of the pricking element which is exposed.

In one preferred embodiment of the lancet assembly of the present invention, the front end of the arm engages with the lancet cover. As a result, after the lancet cover has been removed from the pricking element, the contacting condition of the lancet cover with the arm is maintained by such arm. For example, the front end of the arm has a hooked portion (or an L-shaped portion) which is bent inward, and the lancet cover has a portion on a lateral face thereof which engages with the hooked portion. This constitution makes it possible to restrict the lancet cover, which has been separated from the pricking element, by means of the arm.

In one embodiment of the lancet assembly of the present invention, the lancet holder has a guiding means provided on a side (or lateral) inner wall at the front end thereof;

the lancet cover has a guided means which is guided by the guiding means; and the guiding means and the guided means cooperate so that the lancet cover which has been separated is caused to move forward by the arm which is moving forward while such lancet cover moves obliquely forward (for example, obliquely upward or obliquely downward).

Specifically, the lancet holder has, as the guiding means, a sliding portion which extends along the side inner wall at the front end thereof obliquely forward; and the lancet cover has, as the guided means, a portion (for example, a protruding portion) which slides on the sliding portion.

For example, the lancet cover has, as a slid means, a tapered portion which forward tapers off in the vertical direction along a lateral face of the front end of the lancet cover, and the lancet holder has on a lateral face of the inner wall of the front end of the lancet holder, as the sliding portion, a tapered portion which forward flares (or widens) in the vertical direction (namely, a reverse tapered portion) and on which the former tapered portion moves, so that these tapered portions slide relative to each other, thereby causing the lancet cover which has been separated to move obliquely forward.

In another example, the sliding portion may be a protrusion or a recess which has a sliding surface extending obliquely forward provided on the side-inner wall of the front end of the lancet holder, while the slid portion may be a protrusion provided on the lateral face of the lancet cover, and the latter protrusion is placed on the former protrusion provided on the side inner wall of the front end of the lancet holder or fits into the recess so as to be placed on the slide surface.

It is preferable that the base, the arm, the spring and the connector of the ejector are formed integrally from a resin, and preferably formed integrally by injection molding of a resin. The trigger may also be formed integrally with the ejector. In one preferred embodiment, the components of the ejector other than the trigger are formed in an integral member beforehand as described above, while the trigger component is also formed in advance as a separate component, and the trigger component is combined with thus integrally formed member thereby to obtain the ejector. This combining step can be carried but by fitting a portion of the trigger component into the integrally formed member, specifically fitting into the recess. Preferably a protrusion which can be press-fitted in the recess may be used. The spring may be an independent member made of a metal, in which case ends of the spring may be connected to the base and the connector, respectively.

It is preferable that the lancet body and the lancet cover are preferably formed integrally of a resin as a lancet by inserting a pricking element (typically a needle made of a stainless steel), and preferably formed by injection molding. The lancet cover and the lancet body are connected into an integral piece through a notch portion (for example, a notch portion formed of a resin), which preferably functions as the weakened portion. With regard to this case, the lancet cover and the lancet body may be spaced from each other, with an intermediate portion of the pricking element being exposed between the lancet cover and the lancet body. Alternatively, such intermediate portion of the pricking element may be covered by a readily breakable thin layer of a resin which constitutes the lancet cover and the lancet body (specifically a thin layer which is breakable with a force comparable to that applied upon breaking the notch portion). Such a thin layer can usually be formed when the lancet cover and the lancet body which are connected by the notch portion are formed by the injection molding.

In another embodiment, the lancet cover and the lancet body may be formed as separate members, with the pricking element included in these members. In this case, the lancet cover and the lancet body may be separated, preferably at a distance which is as small as possible, while the intermediate portion of the pricking element is exposed between these members. The ejector and the lancet are separate members, and these members are preferably connected together by the connector provided on the ejector. In other embodiment, the ejector and the lancet may be formed integrally all as a single member, for example, by the injection molding.

The resin that forms the ejector and the lancet, and the lancet holder is preferably one which can be used in the injection molding. Specifically, a polymer material, such as a POM (polyacetal resin), a PBT (polybutylene terephthalate resin), a polyester copolymer resin, an ABS resin, a polycarbonate resin, a polystyrene resin, a polyethylene resin and a polypropylene resin may be exemplified.

In the lancet assembly of the present invention, as the lancet structure is inserted in the lancet holder and the base is moved toward the connector, the spring is compressed with the connector being engaged with and in the lancet holder. This is the connector is once locked by the lancet holder, so that it becomes unable to move further, and thereafter when the base is moved further toward the connector, the distance between the base and the connector decreases so that the spring is compressed. The state of locking the connector by the lancet holder can be maintained by a part of the lancet holder which is to abut against a part of the connector. In one embodiment, the lancet holder has a stopper, for example a protrusion, provided on the inside thereof, and the connector has a portion, for example a protrusion, which can abut against with the protrusion.

Then, when the movement of the base is further continued, the spring is further compressed while the arm moves forward with the lancet body being locked. Accordingly, the lancet cover departs from the pricking element so that the distal end of the pricking element which has been enclosed is finally exposed. Thereafter, the lancet cover moves obliquely forward. As a result, the opening of the lancet holder is positioned directly in front of the distal end of the pricking element.

Then, when the movement of the base is further continued, the trigger of the ejector unlocks the state of engagement as described above of the connector, and therefore of the lancet body. The state of engagement as described above is achieved by a part of the lancet holder which abuts against a part of the connector. That is, those parts press each other in the opposite directions (in the state where the parts press each other with opposite direction forces being applied on the same axis), and therefore the state of engagement of the parts can be easily unlocked by bringing axes of the forces out of alignment. For example, the trigger acts so as to bring the direction, in which the part of the connector applies the force, out of alignment with the direction in which the part of the lancet holder applies the force. Specifically, the connector and the lancet holder are constituted such that the connector has a protrusion extending obliquely upward as said part, and said protrusion abuts against a protrusion formed as said part of the lancet holder. When the trigger moves forward toward the protrusion of the lancet holder, it touches the obliquely extending protrusion of the connector. When the trigger moves further thereafter, the trigger moving forward presses downward the protrusion of the obliquely extending connector, so that the obliquely extending protrusion is gradually moved downward with finally unlocking the state of engagement.

In the lancet assembly of the present invention, the trigger is an elongated member which extends and can move in the pricking direction. By moving in the pricking direction, the trigger presses down the protrusion of the connector with respect to the protrusion of the lancet holder, which protrusions have been in contact and pressing each other in the pricking direction and its opposite direction. Namely, the trigger causes movement of the former protrusion in a direction perpendicular to the pricking direction.

When such trigger unlocks the state of engagement, the spring is released from the compressed state and instantaneously expands, so as to drive the lancet body to move forward, in other words, so as to launch the lancet body having the pricking element of which distal end has been exposed. When a finger tip is placed on the opening positioned at the front end of the lancet holder at this time, the finger is pricked by the distal end of the pricking element. The state of the connector being locked is none other than the state of the lancet body which is connected to the connector being locked. Therefore, a constitution may also be employed wherein the lancet body, instead of the connector, is locked. For example, the lancet body may have a protrusion which is formed preferably at a position near the rear end of the lancet body. In other embodiment, the protrusion as an abutting part may be provided on the spring, particularly near the front end thereof, instead of on the connector.

In the present specification, the terms "front (or forward)" and "rear (or backward)" are used with reference to the direction in which the pricking element moves so as to prick. The terms "upward" and "downward" are used such that the direction along which the lancet cover moves obliquely so as to expose the distal end of the pricking element is referred to as "upward", and the opposite direction is referred to as "downward", based on the plane which is defined by the two arms (namely, the plane which includes the straight lines along which the arms extend while assuming that the arms are extending linearly) and which includes the direction along which the pricking element moves (refer to FIG. 1). The direction which is perpendicular to the front-rear direction and the up-down direction, and which together with these directions, constitutes the orthogonal coordinate system is also referred to as a horizontal direction (right-left direction).

The lancet assembly of the present invention preferably has the lancet structure and the lancet holder described above or to be described later which are combined in any proper configuration. For example, at least a portion of the lancet structure is inserted into the lancet holder. In one more preferred embodiment, the lancet structure as a whole is inserted into the lancet holder, and the connector is locked by the lancet holder, in such a configuration that the protrusion of the connector abuts against the inner protrusion provided inside the lancet holder (the state shown in FIG. 3 as described below, where the spring may not be compressed, or may be compressed a little, FIG. 3 showing the latter state). In this case, as will be described later with reference to FIG. 3, it is particularly preferable that the lancet structure cannot be easily drawn out of the lancet holder. In other aspect, the lancet structure and the lancet holder are not combined. In this case, the present invention may be called, rather than lancet assembly, a kit of the lancet assembly which is to be constituted from the lancet structure and the lancet holder.

In the second aspect, the present invention provides the lancet structure and the lancet holder that constitute the lancet assembly of the present invention described above or to be described later. The present invention also provides the lancet and the ejector which form such lancet structure described above. The descriptions about the lancet assembly of the present invention described above or to be described later are also applied to the lancet structure and the lancet holder as well as the lancet and the ejector.

With the lancet assembly of the present invention, when the lancet structure is inserted into the lancet holder so as to be ready for pricking, the lancet cover is separated from of the lancet body so that the distal end of the pricking element which has been enclosed by the lancet cover is automatically exposed in the holder. Therefore, the action to remove the lancet cover corresponding to the resin cover required with the lancet assembly of the prior art is eliminated. Also, when it is thereafter continued to press the base toward the connector, the lancet is automatically launched while the user is unaware of such launching, and therefore it is not necessary for the user to prepare his or her mind to be ready for the launch.

DETAILED DESCRIPTION OF THE INVENTION

Figure 1:
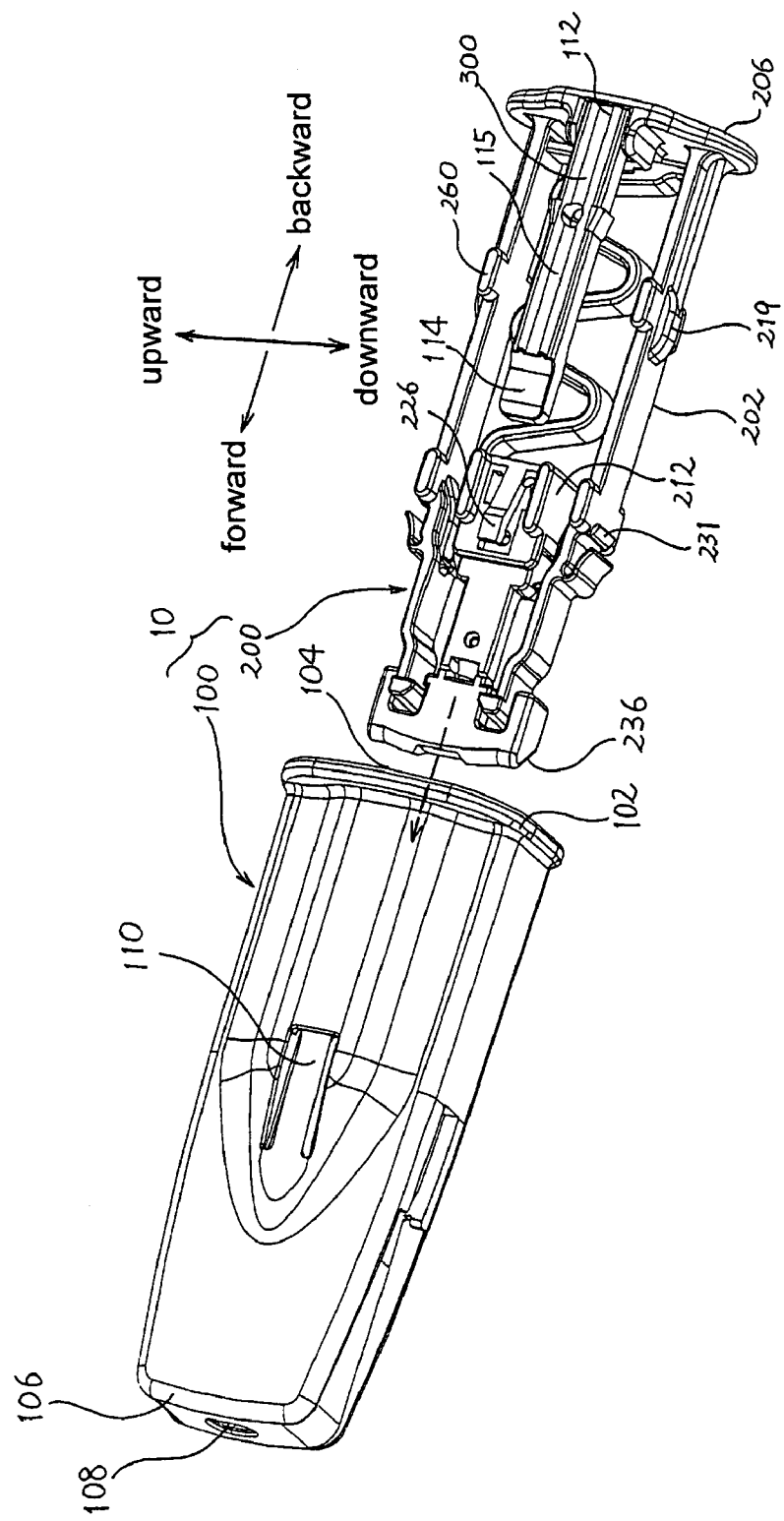
FIG. 1 is a schematic perspective view of the lancet assembly of the present invention before the lancet structure is inserted into the lancet holder.

The lancet assembly 10 of the present invention is shown in the schematic perspective view of FIG. 1. The lancet assembly 10 is constituted from a lancet holder 100 and a lancet structure 200. In the embodiment shown in FIG. 1, the lancet structure 200 is shown in a state immediately before being inserted into the inner space of the lancet holder 100 in the direction indicated by the broken line with an arrow. In FIG. 1, the directions of "front" or "forward", "rear" or "backward", "upward" and "downward" (based on the orthogonal coordinate system) are shown.

The lancet holder 100 has an opening 104 (not shown in FIG. 1) at the rear end 102 thereof, and also has an opening 108 at the front end 106 thereof. With a part of a human body (for example, a finger tip) pressed on to the opening 108, such portion is punctured when the distal end of the pricking element which is exposed is launched from the opening 108. The lancet structure 200 has a trigger 300 provided on the upper side thereof. The rear end 112 of the trigger 300 is connected to a base 206 of the ejector 202. A main body 115 located between the rear end 112 and the front end 114 of the trigger can be pushed into along the inner wall of the lancet holder (in the forward direction in FIG. 1).

Such a constitution is particularly preferable that, as shown in the drawing, the junction between the front end 114 and the main body 115 has a stepped configuration, so that a space 117 (refer to FIG. 11 and FIG. 12) is formed between this part of the trigger and the inner wall of the lancet holder. The lancet holder 100 has a trigger counterpart 110, which opposes to the trigger 300, on the upper side wall thereof, with a part thereof forming a protrusion 116 which protrudes into the inner space of the lancet holder. The protrusion 116 abuts against a connector 212 which will be described later, specifically against a protrusion 226 which extends obliquely forward from the connector, thereby achieving the locking state where the connector 212, and therefore the lancet body 216 connected thereto, is prevented from moving forward. This locking state can be relieved by pressing the front end 114 of the trigger 300 toward a portion where the above mentioned abutting state is formed.

Figure 2:
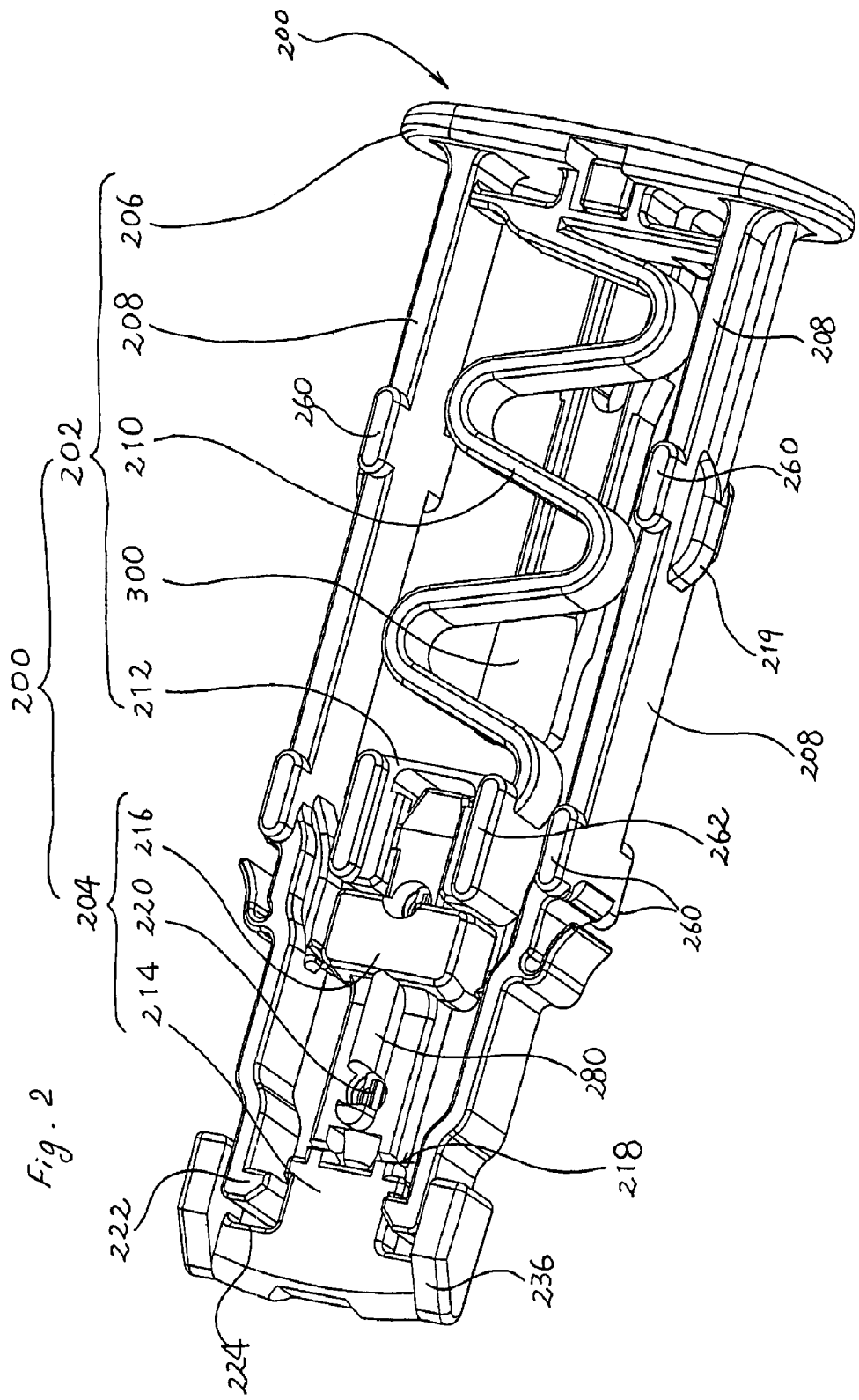
FIG. 2 is a schematic perspective view of the lancet structure which constitutes the lancet assembly of the present invention.
Figure 18:
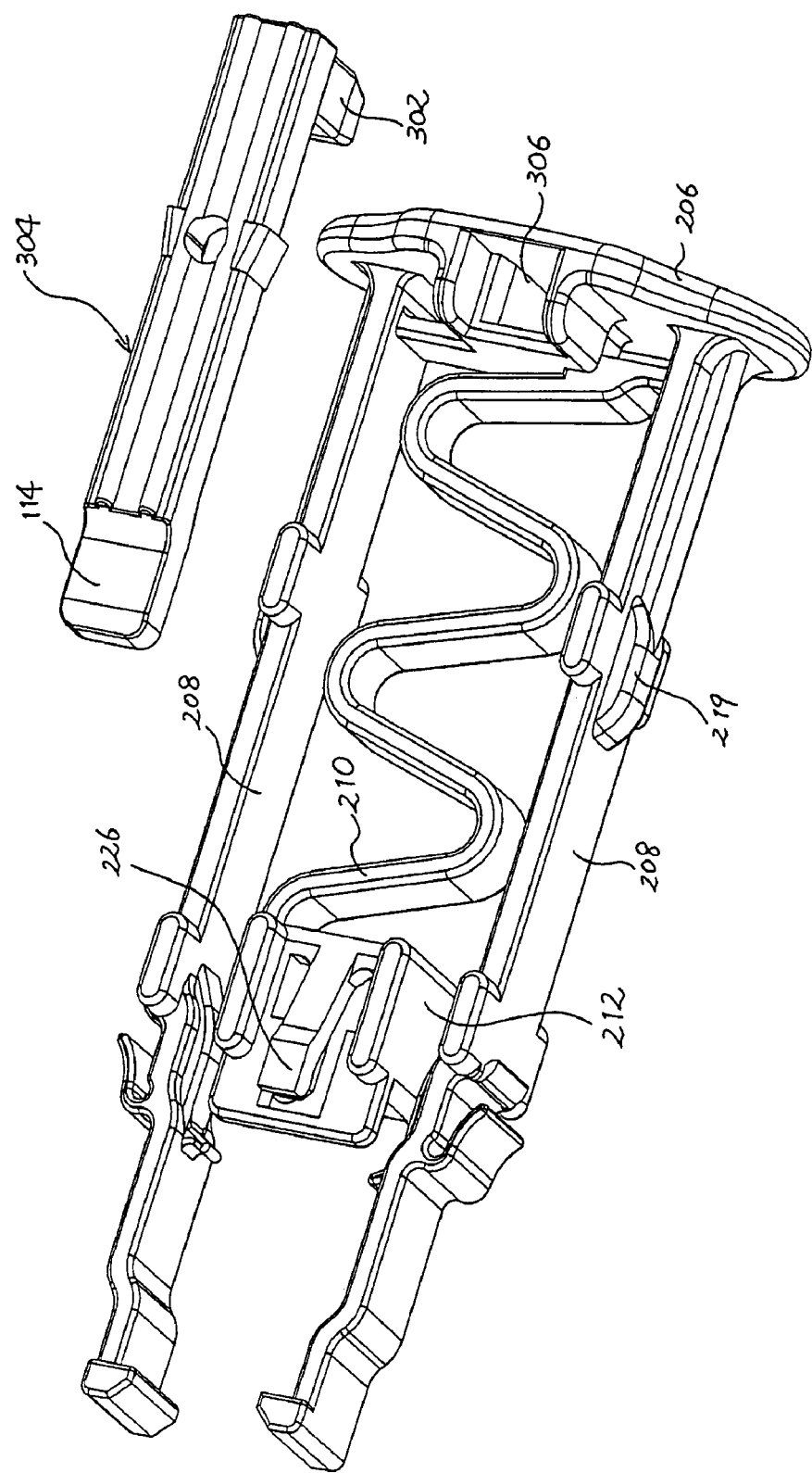
FIG. 18 is a schematic perspective view showing a trigger element fitted in the base of the ejector so as to constitute the ejector.

FIG. 2 is a schematic perspective view of the lancet structure 200 shown in FIG. 1 with the up and down sides of the lancet structure reversed (namely, upside down). The lancet structure 200 is constituted from the ejector 202 and the lancet 204. The ejector 202 has the base 206, and arms 208 are provided on both end portions thereof. While it is preferable that a spring is provided between a pair of arms, the number of the arms may be one or three or more. The spring 210 having a corrugated shape is disposed between the arms, and one end of the spring is attached to the base 206. In the embodiment shown in the drawing, the spring 210 is connected also to the arm 208 at the foot of the arm 208 which is connected to the base. Thus the end of the spring 210 is connected to the arm and/or the base. Attached to the other end of the spring 210 is a connector 212. As described above, the base 206, the arm 208, the spring 210 and the connector 212 are preferably formed into an integral piece, for example, by the injection molding of a resin. The trigger 300 is preferably formed by combining a trigger element formed as a separate element with the other integral element that constitutes the ejector. Specifically, the trigger element 304 having a projection 302 is formed in advance as shown in FIG. 18. A recess 306 having a form complementary to the projection is provided in the base 206 of the ejector. The ejector of the present invention is preferably constituted by fitting the projection 302 into the recess 306, preferably by press fitting. The spring may be provided as a separate member, and for example, it may be a spring made of a metal.

The lancet 204 is constituted from the lancet body 216 and the lancet cover 214, which are connected to each other by a weakened portion 218 constituted in the form of a notch portion (for example, a V-shaped recess). The lancet 204 has also a pricking element 220, while the distal end of the pricking element is enclosed by the lancet cover 214 so that such end is sealed. The rear portion of the pricking element 220 is disposed within the lancet body 216. In the embodiment shown in the drawing, while a part of the pricking element 220 may be exposed between the lancet body 216 and the lancet cover 214, such part may also be covered by a resin as in the shown embodiment, and at least a portion of such covering resin thereof has a form of a thin layer so as to be easily broken when the lancet body and the lancet cover are separated from each other by applying a force with fingers. In other embodiment, the lancet body and the lancet cover may be spaced from each other as independent members without the weakened portion provided therebetween. The spaced distance between the members is preferably as small as possible, and preferably near zero.

As can be seen from the drawing, the lancet cover 214 is positioned in front of the arms 208 and, in the shown embodiment, the front ends 222 of the arms 208 are positioned proximate to the rear end 224 of the lancet cover 214. In other embodiment, these members (i.e. the front ends 222 and the rear end 224) may be in contact with each other without being spaced. In the embodiment in which these members are disposed close to each other, too, the front ends 222 of the arms 208 abut against the rear end 224 of the lancet cover 214 when the arms 208 are moved further forward after the forward movement of the lancet body 216 has been stopped, as will be described later.

Figure 3:
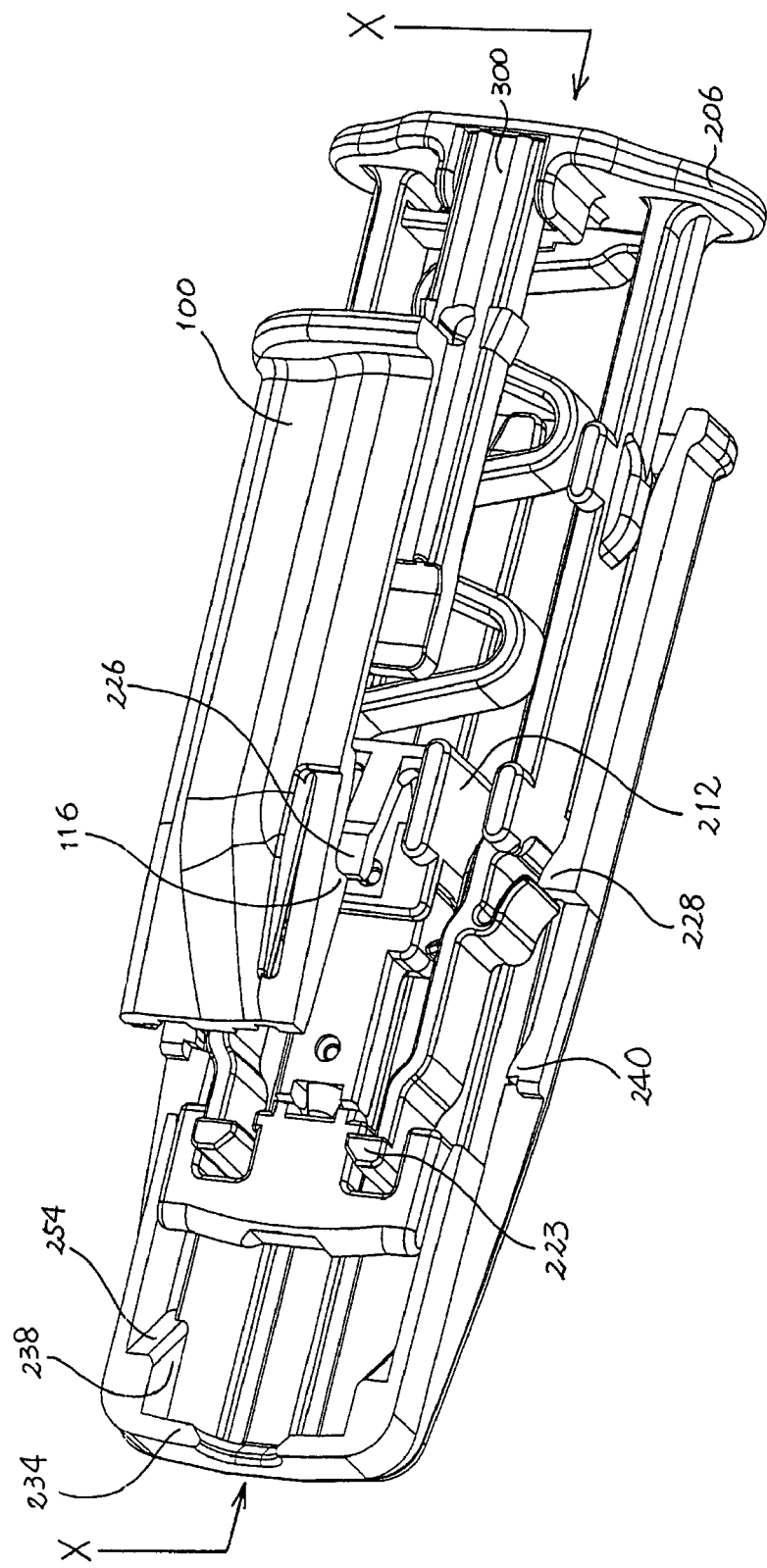
FIG. 3 is a schematic perspective view of the lancet assembly of the present invention in the state that the lancet structure is inserted into the lancet holder and forward movement of the lancet body is restricted.

The state of the lancet structure 200 having been inserted into the lancet holder 100 as described above is shown in the schematic perspective view of FIG. 3. To make it easier to understand the state of the lancet structure in the lancet holder 100, the lancet holder is shown in the drawing as partially cut away leaving the lower half of the lancet holder and the rear half of the distal side half of the upper portion of the lancet holder. When the lancet structure 200 is inserted from the state shown in FIG. 1, the protrusion 226 of the connector 212 which protrusion extends obliquely upward and forward abuts against the protrusion 116 of the trigger counterpart 110 of the lancet holder 100 which protrusion extends downward or downward and backward.

In the shown embodiment, the protrusion 228 having a taper-like shape of which width in the horizontal direction (the direction which is perpendicular to the front-rear direction and the up-down direction in FIG. 1) increases forward is provided on each lateral side of the inner wall of the lancet holder, so that in the course of inserting the lancet structure 202, a wing or flap 230 (preferably having a thin layer form) which extends from the arm obliquely rearward and which is provided at an in-between position of each arm 208 can move forward while getting over the protrusion 228. The protrusion 228 is positioned preferably such that the protrusion 226 just comes into contact with the protrusion 116 when the wing 230 gets over the protrusion 228. In other embodiments, the wing may get over the protrusion 228 before or after such coming into contact. A taper-like protrusion (thinning forward) may also be used instead of the wing 230.

Use of the wing configuration makes it possible to make use of the elasticity of the wing material (for example, a resin material), and also make the wing 230 get over the protrusion 228 easily while, after getting over, making it substantially impossible for the wing 230 to move back by getting over the protrusion 228. It may be advantageous to use the tapered protrusion described above which makes a stronger snapping touch than in the case of using the wing when getting over the protrusion, so that therefore makes the person who assembles the assembly or the user of the assembly can be aware that coming into contact has been achieved. Such a movement of getting over can also be achieved by forming the lancet structure and the lancet holder, particularly the protrusions thereof, from a resin and taking advantage of the elasticity of such resin. Similarly, use of the taper-like protrusion makes it substantially impossible for the protrusion 230 to move back by getting over the protrusion 228, after having got over the protrusion 228. As a result, once the state shown in FIG. 3 has been achieved, it becomes difficult to draw out the lancet structure from the lancet holder, as described previously. In either case, it becomes substantially impossible to disassemble the assembly (namely to draw out the lancet structure from the lancet holder) after setting up or using the lancet assembly, so that reuse or mishandling of the assembly is avoided so as to ensure the safety.

It is preferable that the arm 208 has a protrusion 219 on the outside thereof as shown in the drawing. The protrusion 219 moves sliding along the inner wall of the lancet holder, so as to prevent most part of the arm 208 from making contact with the inner wall of the lancet holder. As a result, it becomes easier to insert the lancet structure into the lancet holder. While it is preferable that the protrusion 219 partially extends along the direction along which the arm extends as shown in the drawing, the protrusion 219 may also be formed in a dot shape (or a cylinder of small height).

Figure 16:
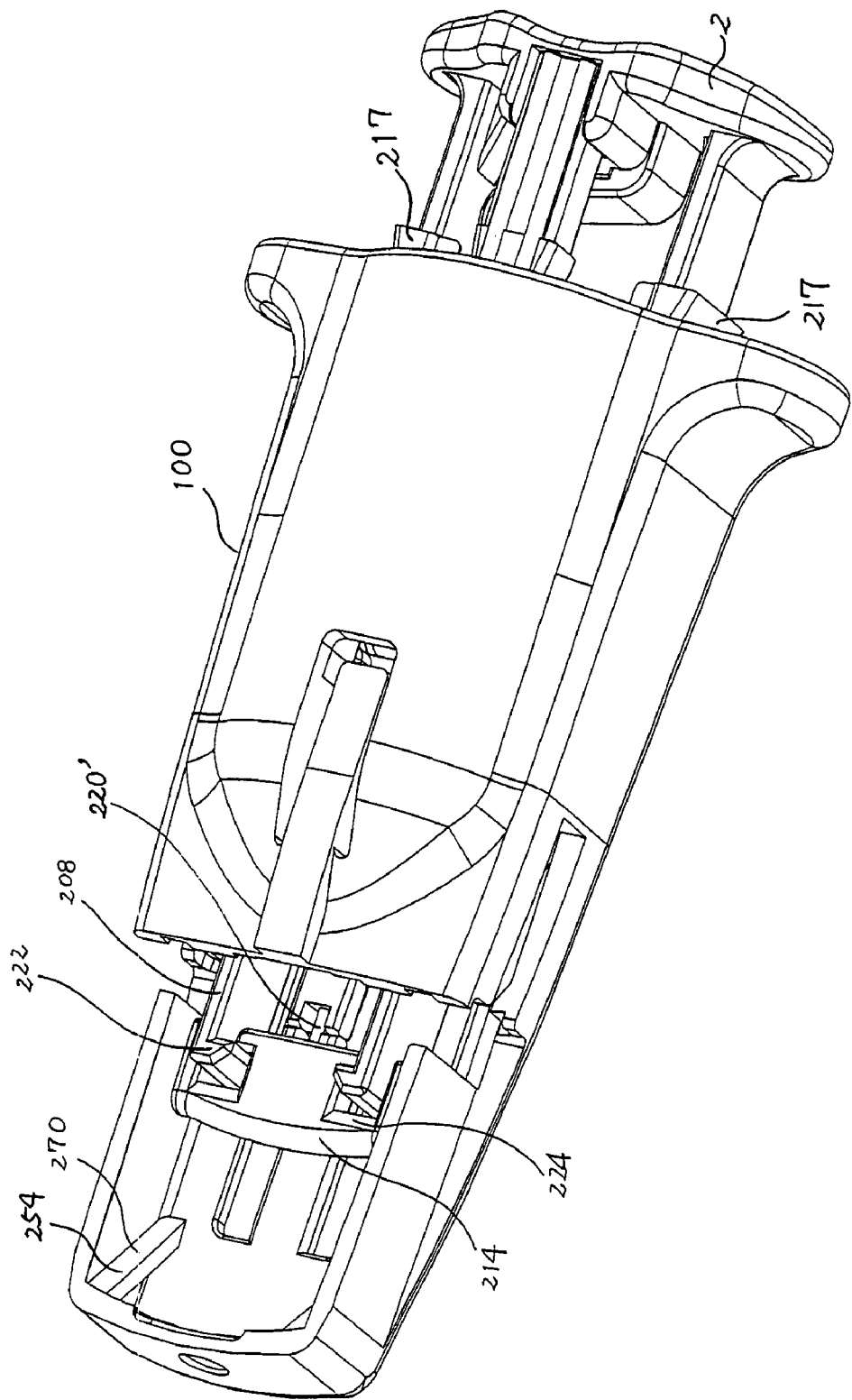
FIG. 16 is a schematic perspective view similarly to FIG. 3, showing other embodiment where the lancet cover is moved obliquely forward.
Figure 17:
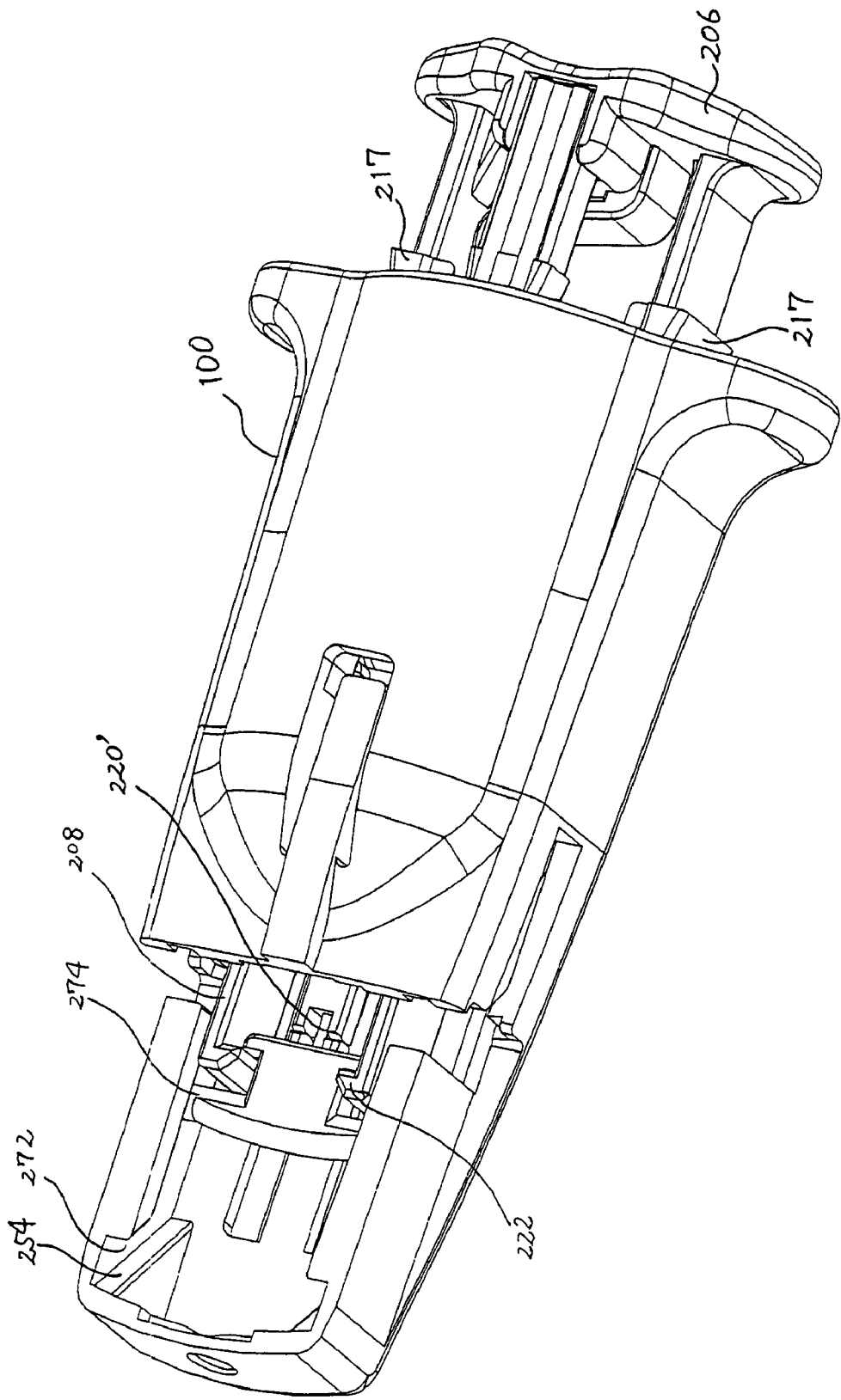
FIG. 17 is a schematic perspective view similarly to FIG. 3, showing a further embodiment where the lancet cover is moved obliquely forward.

It is also preferable that the arm 208 has other protrusion 217 (refer to FIG. 16 and FIG. 17). The protrusion 217 is preferably disposed such that the user can see it and know that the protrusion 217 is positioned outside of the lancet holder 100 and adjacent to the opening 104, when the lancet structure 200 was inserted into the lancet holder 100 and the protrusion 230 has got over the protrusion 228 as shown in FIG. 3. When the protrusion 217 is positioned in this way, the user can know at a glance that the lancet assembly has not been used yet. When the user cannot see the protrusion 217 because the protrusion 217 is disposed within the lancet holder, this means that there is a possibility that the lancet assembly has been used. As will be described later, this is because when the lancet structure 100 is pressed into from the state shown in FIG. 3, the protrusion 217 is concealed and the lancet is launched, thus the lancet assembly is put into its used condition. Of course, there is such an exceptional situation that pressing motion is stopped just before launching, in which case the lancet assembly has not been used although the protrusion 217 cannot be seen.

Figure 4:
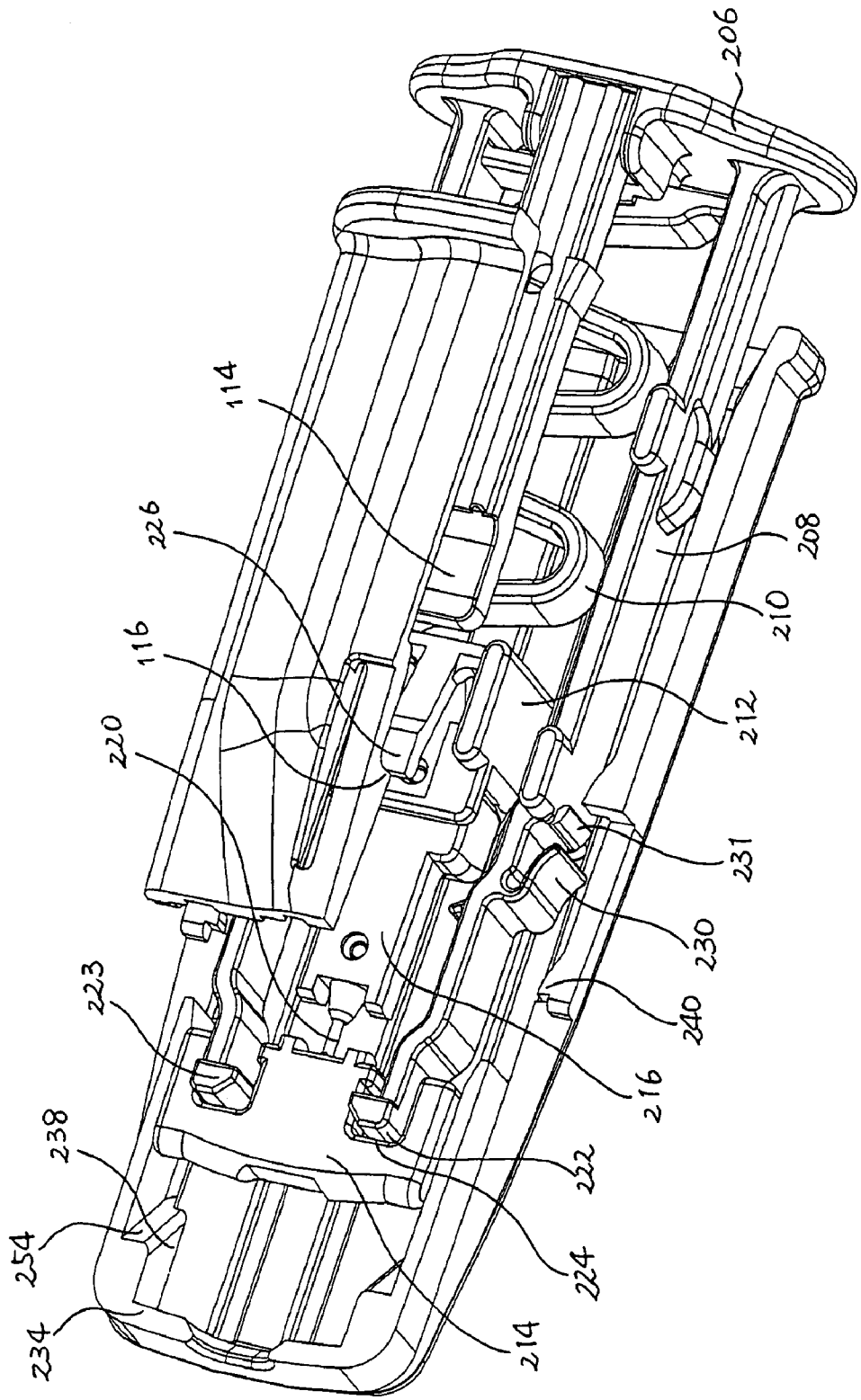
FIG. 4 is a schematic perspective view of the lancet assembly of the present invention in the state that the lancet structure is inserted further from the state shown in FIG. 3, so that the lancet cover is separated from the lancet body.

A subsequent state after applying a force to the base 206 so as to move the lancet structure 200 forward and thus insert the lancet structure 200 further is shown in FIG. 4. As will be clear from comparison with FIG. 3, the base 206 has been moved forward and the arms 208 also have been moved forward since the spring 210 can be compressed in FIG. 4, while the connector 212 cannot move forward because it is abutting against the protrusion 116 and therefore the connector 212 is located at the same position as in FIG. 3.

Figure 5:
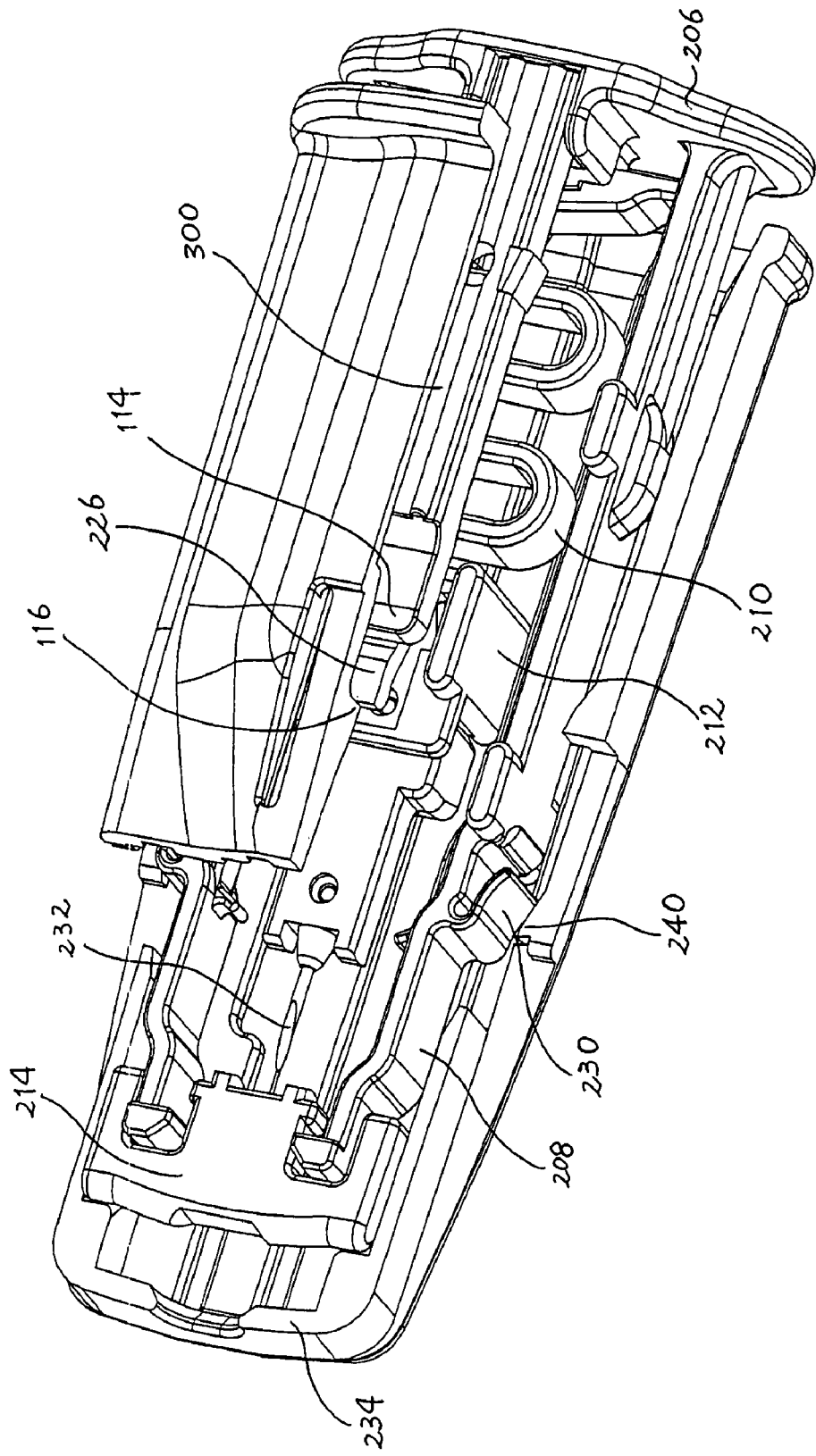
FIG. 5 is a schematic perspective view of the lancet assembly of the present invention in the state that the lancet structure is inserted further from the state shown in FIG. 4, so that the lancet cover has moved away from the lancet body.

In the state shown in the drawing, the protrusion 116 and the protrusion 226 receive the forces which press in the opposite directions along the same axis. Therefore, when the base is pressed into further in this state so as to cause the trigger 300 to move further forward in the lancet holder, the front end 114 of the trigger 300 abuts against the protrusion 226 which extends obliquely upward as shown in FIG. 5. Then, when the trigger 300 is moved further forward, the front end 114 presses downward (see the arrow in FIG. 12) the protrusion 226 of the connector which extends obliquely, so that the pressing forces are brought out of the alignment thereby causing the protrusion 226 which extends obliquely upward from the connector 212 to be gradually directed downward.

When the lancet structure 200 is pressed into further from the state shown in FIG. 3, the front ends 222 of the arms 208 abut against the back side 224 of the lancet cover 214. Then, the arms 208 apply a force to the lancet cover 214 such that moves the lancet cover 214 is moved forward. On the other hand, the connector 212 is unable to move forward because the protrusions 116 and 226 are abutting against each other. Thus, a force acts such that the lancet cover 214 and the lancet body 216 are connected to the connector 212 are separated from each other. As a result, the thin resin layer between the lancet cover 214 and the lancet body 216 is broken and these members are pulled apart into the state shown in FIG. 4.

Then, when the lancet structure 200 is pressed into further from the state shown in FIG. 4, the distal end 232 of the pricking element 220 is exposed as shown in FIG. 5. In an embodiment in which the lancet body and the lancet cover are separate members, the lancet body moves away from the lancet cover so that the distal end of the pricking element is eventually exposed.

Figure 6:
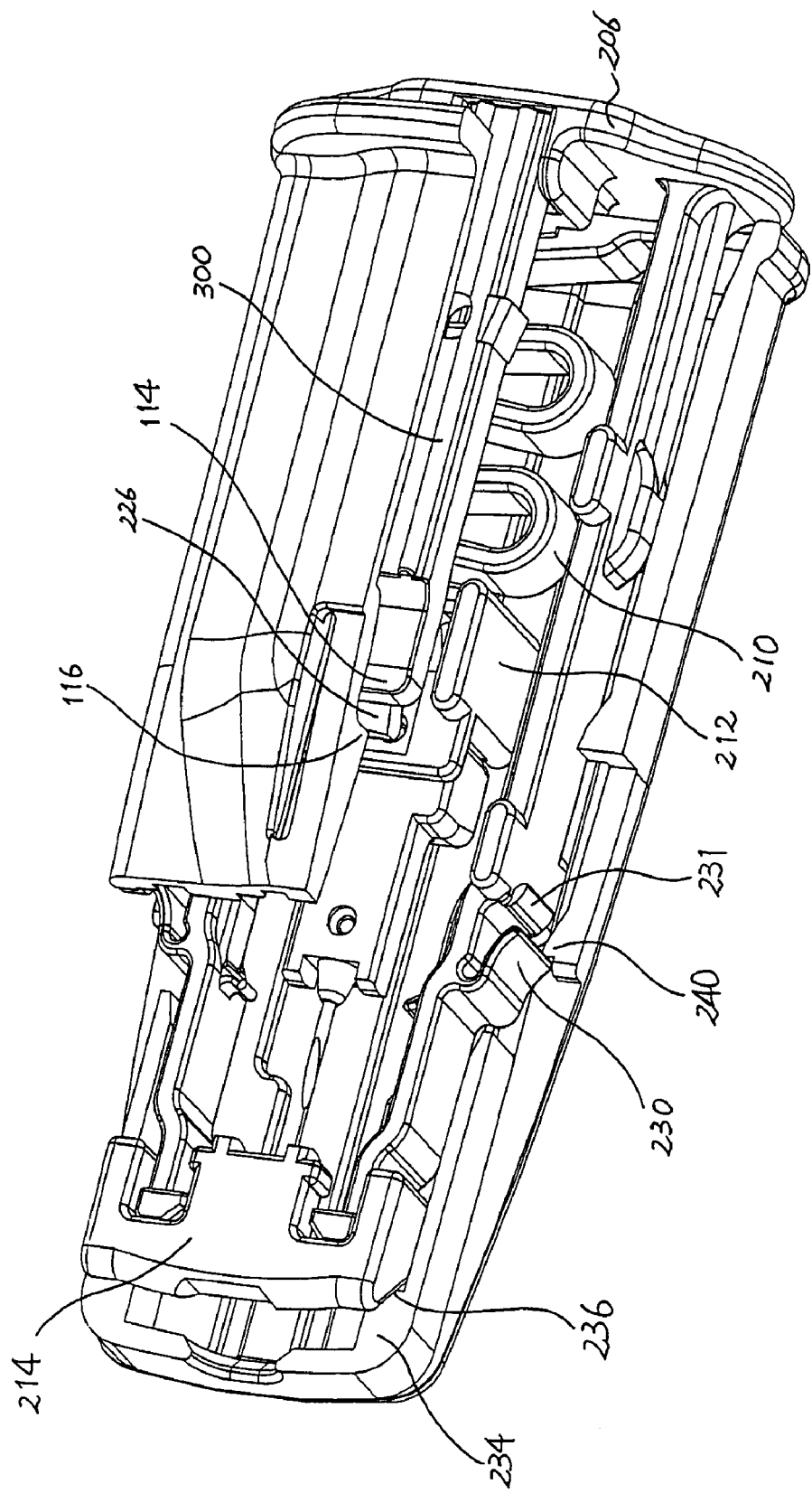
FIG. 6 is a schematic perspective view of the lancet assembly of the present invention in the state that the lancet structure is inserted further into lancet holder from the state shown in FIG. 5, so that the lancet cover has moved forward obliquely upward and is being held in the front end of the lancet holder (the state just after the abutting state of the protrusions against each other has been relieved).

A state of applying a force to the base 206 is shown in the schematic perspective view of FIG. 6 in order to move the lancet structure 200 forward and insert the lancet structure 200 further from the state shown in FIG. 5 in which the distal end of the pricking element is exposed. FIG. 6 shows the state that the front end 114 of the trigger 300 which has been moved forward by inserting the lancet structure 200 presses the protrusion 226 of the connector downward, whereby the abutment state of the protrusion 226 against the protrusion 116 has just released. As will be clear from comparison with FIG. 5, while the arms 208 have moved further forward, the protrusion 226 is abutting against the protrusions 116, so that the connector 212 is unable to move forward unless the abutment state is released. In FIG. 6, the state immediately after the abutment state has been released is shown, and therefore the position of the connector 212 is substantially the same as that in the previous state of not having been moved forward. Since the spring 210 is compressible, it is more compressed in the state shown in FIG. 6 than in the state shown in FIG. 5, and the base 206 has been moved further forward. In the shown embodiment, the protrusion 226 is provided on the connector 212, although the protrusion may be provided on the spring 210 (particularly on the front end thereof) or on the lancet body 216.

As will be easily understood from FIGS. 3, 4, 5 and 6, the lancet assembly of the present invention preferably has a constitution such that the front ends of the arms can engage with the lancet cover. More specifically, the front end 222 of each arm 208 has a hooked portion (or L-shaped portion) which is bent inward, and the lancet cover 214 defines a portion 225 provided on each lateral face thereof which can engage with the hooked portion. In the shown embodiment, such portion defines a complementary shape 225 into which the hooked portion 223 fits (refer to FIG. 9). When the front ends of the arms engage with the lancet cover, the abutting state between the front ends 222 of the arms 208 and the lancet cover 214 is maintained by such engagement even after the pricking element 220 has been separated from the lancet cover 214. As a result, in the state shown in FIG. 5 where the distal end 232 of the pricking element is exposed, the lancet cover 214 can be moved backward together with the arms 208 even when the arms 208 are moved back somewhat due to the action of the spring 210 by for example inadvertently removing the force that presses the base 206. In the case wherein such engagement cannot be maintained, the arms moving back bring the lancet cover in a free state, so that it may become difficult to ensure the abutment state between the front ends 222 of the arms 208 and the lancet cover 214 when the arms are moved forward thereafter. It is of course definite that a form other than the hooked shape may be used as long as the front ends of the arms can engage with the lancet cover.

What is to be noted in the lancet assembly of the present invention is that the lancet holder has a guiding means or guide provided on the side inner wall in the front end thereof, while the lancet cover has a guided means which is guided by the guiding means or guided device, so that when the guiding means and the guided means cooperate with each other, the lancet cover moves forward and obliquely (obliquely upward or obliquely downward) when the lancet cover which has been separated is pushed forward by the arm(s) which is moved forward. More specifically, the lancet holder has, as the guiding means, a sliding portion which extends obliquely forward on the side inner wall in the front end thereof, and the lancet cover has, as the guided means, a portion such as a protrusion which is slid over the sliding portion.

In the embodiment shown in FIG. 6, after the states shown in FIGS. 4 and 5, the lancet cover 214 which has been separated is pushed by the arms 208 to move forward, thereby abutting against the inside of the front wall 234 of the lancet holder. Provided as the guided means on each side of the lancet cover 214 is a tapered portion 236 of which width in the vertical direction decreases forward. Provided as the guiding means on each side inner wall of the front end of the lancet holder 100 is a tapered portion 238 of which width in the vertical direction increases forward (namely, a reverse tapered portion), and the reverse tapered portion 238 as the guide means has, as the sliding means, an inclined surface 254 (refer to, for example, FIG. 3). These tapered portions are constituted such that the bottom surface of the tapered portion 236 slides on the inclined surface 254. FIG. 5 shows a state immediately before such sliding motion begins. As a result, the tapered portion 236 of the lancet cover 214 which is pushed forward by the arms 208 moves upward along the inclined surfaces 254 of the reverse tapered portions 238. That is, in the state shown in FIG. 6, the lancet cover 214 has been caused by the arms 208 to move forward and obliquely upward so as to abut against the inside of the front wall 234 of the lancet cover. This abutting state of is maintained by keeping the condition of being pushed by the arms 208.

The movement of the lancet cover in the oblique direction in one embodiment may be achieved in such a constitution that the sliding portion is a projection or an inclined plate 270 which is provided on the side inner wall of the front end of the lancet holder and also which has a sliding surface extending obliquely forward as shown in FIG. 16, and the slid portion is the lateral portion of the lancet cover 214 or a protrusion (which is similar to the protrusion shown in FIG. 15 which will be described later) provided on the lateral portion.

In a further embodiment, the sliding portion has a form of a recess 272 which is provided on the side inner wall of the front end of the lancet holder and also which has a sliding surface extending obliquely forward, and the slid portion is a protrusion or an extension 274 provided on the lancet cover, while such protrusion fits and is guided in the recess.

FIGS. 16 and 17 are schematic perspective views of the states corresponding to FIG. 3, in other preferred embodiments of the lancet assembly according to the present invention shown in FIGS. 1 to 15. In those drawings a portion 2201 of the pricking element is exposed between the lancet cover and the lancet body, and the arm 208 has the protrusion 217 as described above.

It is necessary that the movement of the lancet cover 214 in the oblique direction as described above is enough to allow the distal end 232 of the exposed pricking element to prick a finger tip or the like through the opening 108 positioned at the front end of the lancet holder 100. That is, when the lancet body 216 of which the distal end 232 of the pricking element is exposed is launched, the lancet cover 214 never exists in front of the distal end 232 along the direction of movement of the distal end, so that the lancet cover 214 never contacts with the distal end 232 so as not to impede the movement of the distal end (namely, the lancet cover 214 does not exist in the trajectory of the distal end 232). The term "directly" has been used in the above in this sense.

When the lancet cover 214 is kept in the above of the inside of the front wall of the lancet holder 100 as described above, the preparation for the pricking operation is completed. In this case, similarly to that described previously, the taper-like protrusion 240 of which width in the horizontal direction increases forward is provided on the lateral face of the inner wall of the lancet holder (between the protrusion 228 described above and the front end of the lancet holder), so that in the course of inserting the lancet structure 200, the wing or protrusion 230 which is provided at an in-between position amid of the arm 208 can get over the protrusion 240. The protrusion 240 is positioned preferably at a position such that the lancet cover 214 just comes into contact with the inside of the front wall 234 of the lancet holder when the wing or the protrusion 230 has got over the protrusion 240. In other embodiment, such coming into contact may be achieved immediately before the wing gets over the protrusion 240, and the lancet is launched at the same time as such getting over (that is, the state shown in FIG. 6).

With the wing or the protrusion 230 and the protrusion 240 provided as described above, descriptions similar to the descriptions given previously with reference to the protrusion 228 are applicable also to this case.

The preparation for the pricking operation is completed at a time immediately before the state shown in FIG. 6 is achieved (namely, the state when the front end of the trigger 300 is positioned a little behind the position shown in FIG. 6, and slight contact is achieved between the protrusion 116 and the protrusion 226 in the state shown in FIG. 6). As will be clear, in the state of being ready for pricking, while the protrusion 226 of the connector 212 to which the lancet body 216 is connected remains in contact with the protrusion 116 of the lancet holder which protrusion is positioned in front of the trigger 300, the region over which both protrusions make contact with each other clearly decreases, and slight contact between them is maintained since the protrusion 226 is gradually pressed downward (refer to the arrow in FIG. 12) as described previously. When the trigger is moved further forward from this state, the protrusion 226 moves further downward so that the contact region eventually diminishes. That is, the forces of the protrusion 116 and the protrusion 226 pressing each other are brought completely out of the alignment, thus breaking the engagement state so as to reach the state shown in FIGS. 6 and 13.

As a result, as the compressed spring 210 restores its original shape, the connector 212, and therefore the lancet body 216 having the pricking element of which distal end is exposed is launched forward. Since the distal end 232 can protrude from the opening 108 without being hampered by the lancet cover 214, the pricking operation can be performed. The situation of the distal end which is protruding is shown schematically in the perspective view of FIG. 7. The spring 210 is instantaneously released from the state of being restrained while being compressed, and is therefore shown elongated in the state shown in FIG. 7 in comparison to the state shown in FIG. 2.

Figure 8:
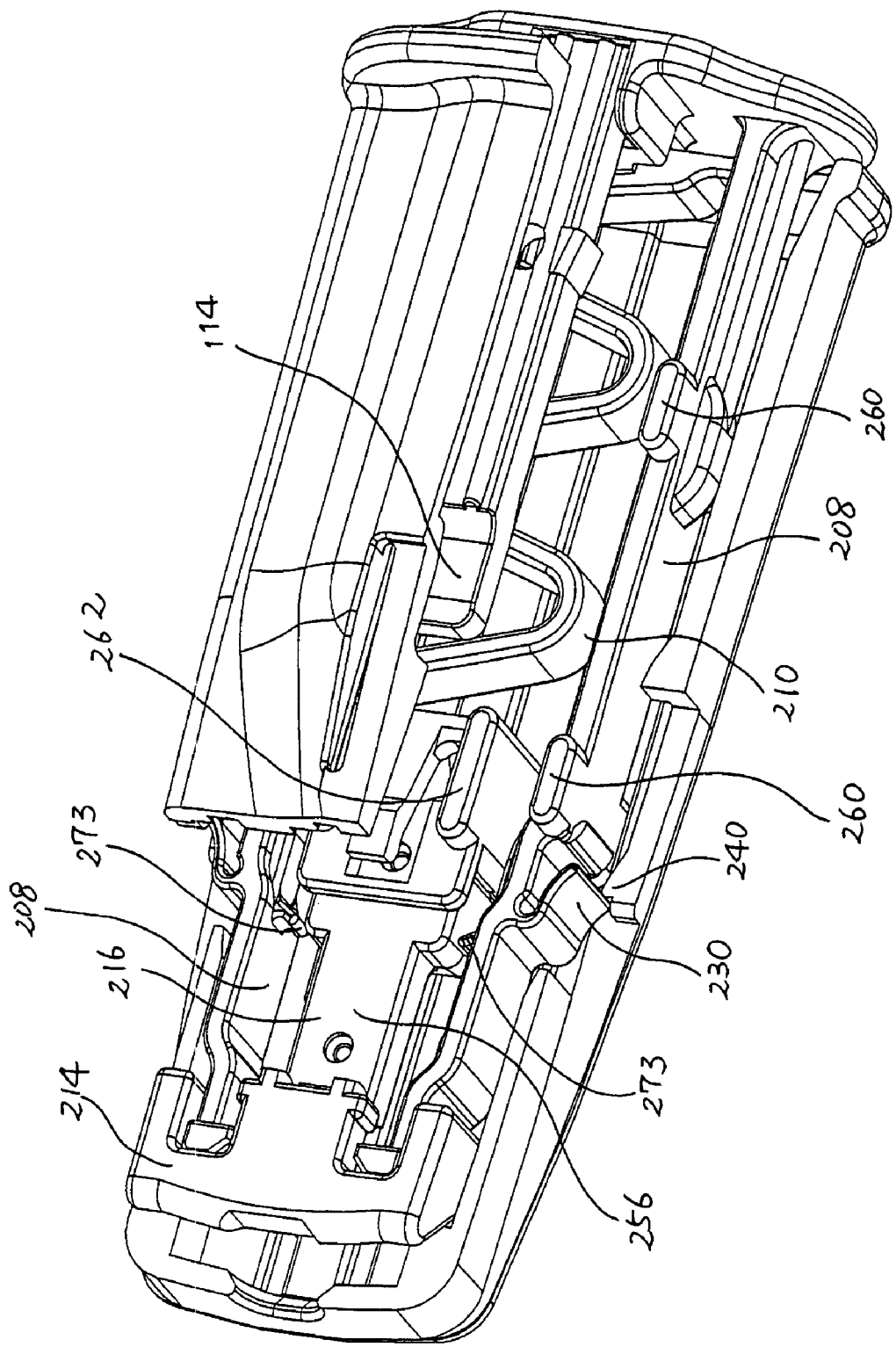
FIG. 8 is a schematic perspective view of the lancet assembly of the present invention in the state that the spring has restored its original shape from the state shown in FIG. 7, and the distal end of the pricking element is retracted inward from the opening positioned at the front end of the lancet holder to the inside.

When the distal end 232 of the pricking element protrudes from the opening 108, the predetermined position is pricked while the front portion 256 of the lancet body 216 collides with the front wall of the lancet holder. As a result, the spring 210 which has expanded is caused to restore its original shape by the reactive force so as to finally return to the shape similar to that in the state shown in FIG. 2. This situation is shown in FIG. 8. In the state where the spring 210 restored its original shape, the distal end 232 of the pricking element is positioned inward by a sufficient distance from the opening 108 of the lancet holder (the position of the distal end is located below the lancet cover 214 and therefore it is not seen in FIG. 8). As a result, it is possible to effectively avoid a situation wherein the distal end 232 of the pricking element, which has been exposed through the opening 108, can be touched from the outside of the lancet holder 100.

Figure 7:
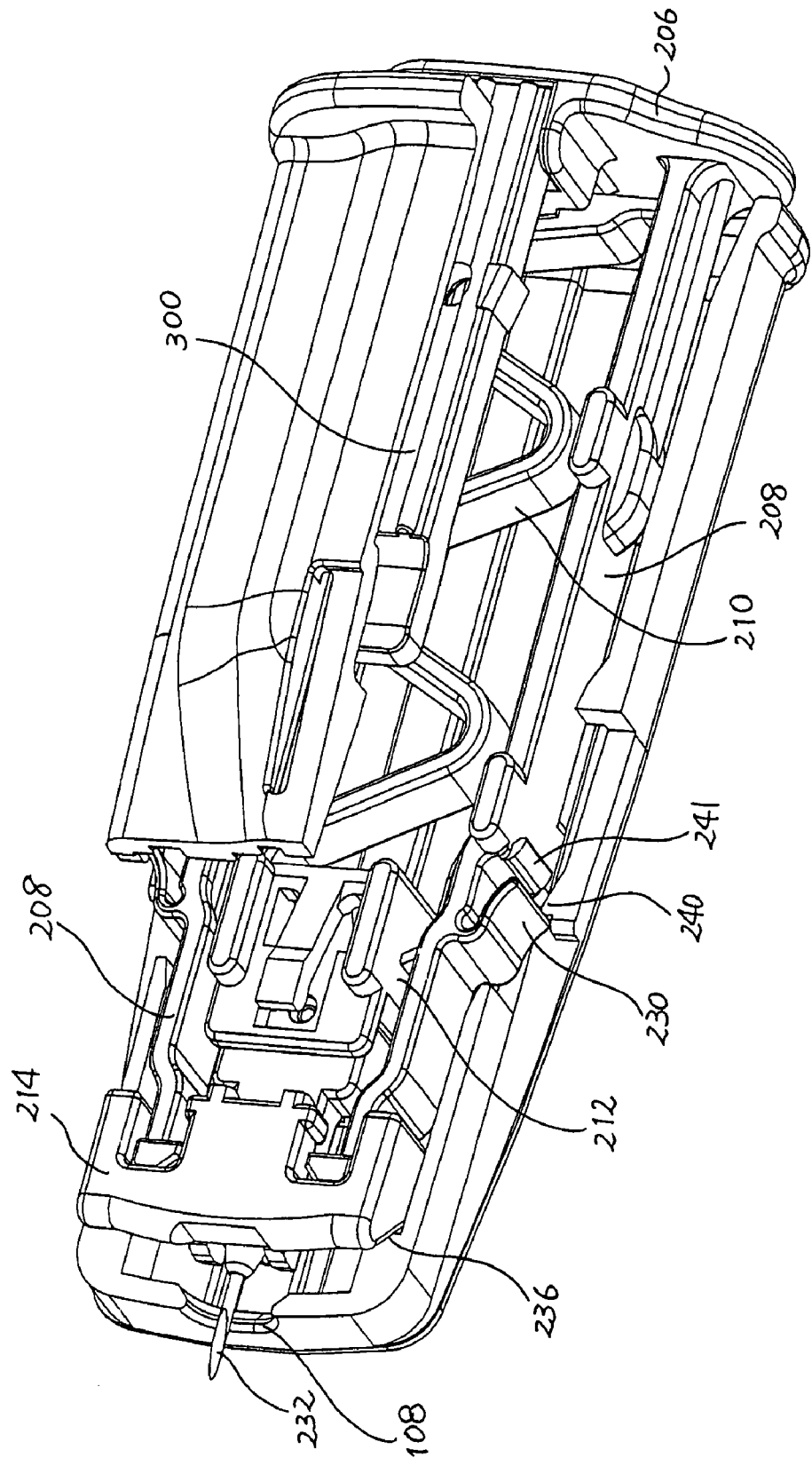
FIG. 7 is a schematic perspective view of the lancet assembly of the present invention in the state that the lancet body is released from its restriction of the state shown in FIG. 6 so that the distal end of the pricking element protrudes from the opening positioned at the front end of the lancet holder.

FIG. 8 shows the state where the pricking operation by the lancet assembly has been completed, and therefore the assembly may be disposed as in the state shown in FIG. 7. As described previously, providing the protrusions 230 and 240 having the wing or tapered configuration makes it impossible to draw the lancet structure 200 from the lancet holder 100 in the state shown in FIG. 8. As a result, the distal end of the pricking element will never be exposed even when the assembly is discarded as in the state shown in FIG. 8. Thus, inadvertent contact with the distal end can be avoided and safety upon the disposal is improved.

As shown in the drawing, it is preferable that the arm 208 further has a protrusion, preferably a taper-like protrusion 231 (which tapers off) provided behind the wing or the protrusion 230. Since the state shown in FIG. 8 is achieved after launching the lancet wherein the wing 230 is engaged with the protrusion 240, it is not easy for the lancet structure to move backward from the position shown in FIG. 8 in the lancet holder 100, as described previously. However, there is a possibility of the wing 230 to deform and, if this is the case, the wing 230 may move backward while by getting over the protrusion 240. In such a case, if another protrusion 231 exists behind the wing 230, this protrusion is not substantially capable of getting over the protrusion 238 positioned behind thereof. As a result, with the used lancet assembly, the lancet structure of which the pricking element 220 is exposed cannot be drawn out of the lancet holder 100.

In a preferred embodiment, each of the arms 208 is constituted to have a protrusion 260 as a guide pin as shown in the drawing. The guide pin is constituted so as to cooperate with a channel which is provided on the inner surface of the lancet holder and extends in the pricking direction. That is, when the lancet structure is inserted into the lancet holder, the guide pin moves while sliding in the channel so that the arm moves forward smoothly in the lancet holder, thereby making the insertion more smooth. In other words, the guide pin induces forward movement of the arm in the lancet holder. Such guide pin(s) may also be provided on the upper side and/or the lower side of the arm.

In other preferred embodiment, the connector 212 has a protrusion 262 as a guide pin as shown in the drawing. The guide pin cooperates with other channel which is provided on the inner surface of the lancet holder and extends in the pricking direction. That is, when the lancet structure is inserted into the lancet holder, the guide pin moves while sliding in the channel so that the lancet body moves forward smoothly in the lancet holder, thereby making the insertion more smooth. The channel also makes it smoother for the lancet body 216 to move forth and back in the puncturing direction within the lancet holder when the lancet body 216 is launched and the pricking operation is carried out, and the distal end of the pricking element is retracted thereafter. In other words, the guide pin induces launching of the lancet body which has the exposed pricking element. The guide pin(s) may also be provided on the upper side and/or the lower side of the arm.

The lancet structure of the present invention is constituted from the ejector 202 and the lancet 204, which are connected integrally via the connector 212. These members may be connected by any proper means. For example, of a set of a recess (a female member or a key hole member) and a protrusion (a male member or a key member) which can be fitted with each other (preferably having shapes complementary to each other), one is formed on the connector 212 and the other is formed on the lancet body 216. When forming the recess and the protrusion, the recess is formed on the connector and the protrusion is formed on the lancet body (or vice versa) such that the lancet body and the connector are engaged with each other and cannot be separated in the front and back direction but can be fitted (or separated) in the vertical direction.

Figure 9:
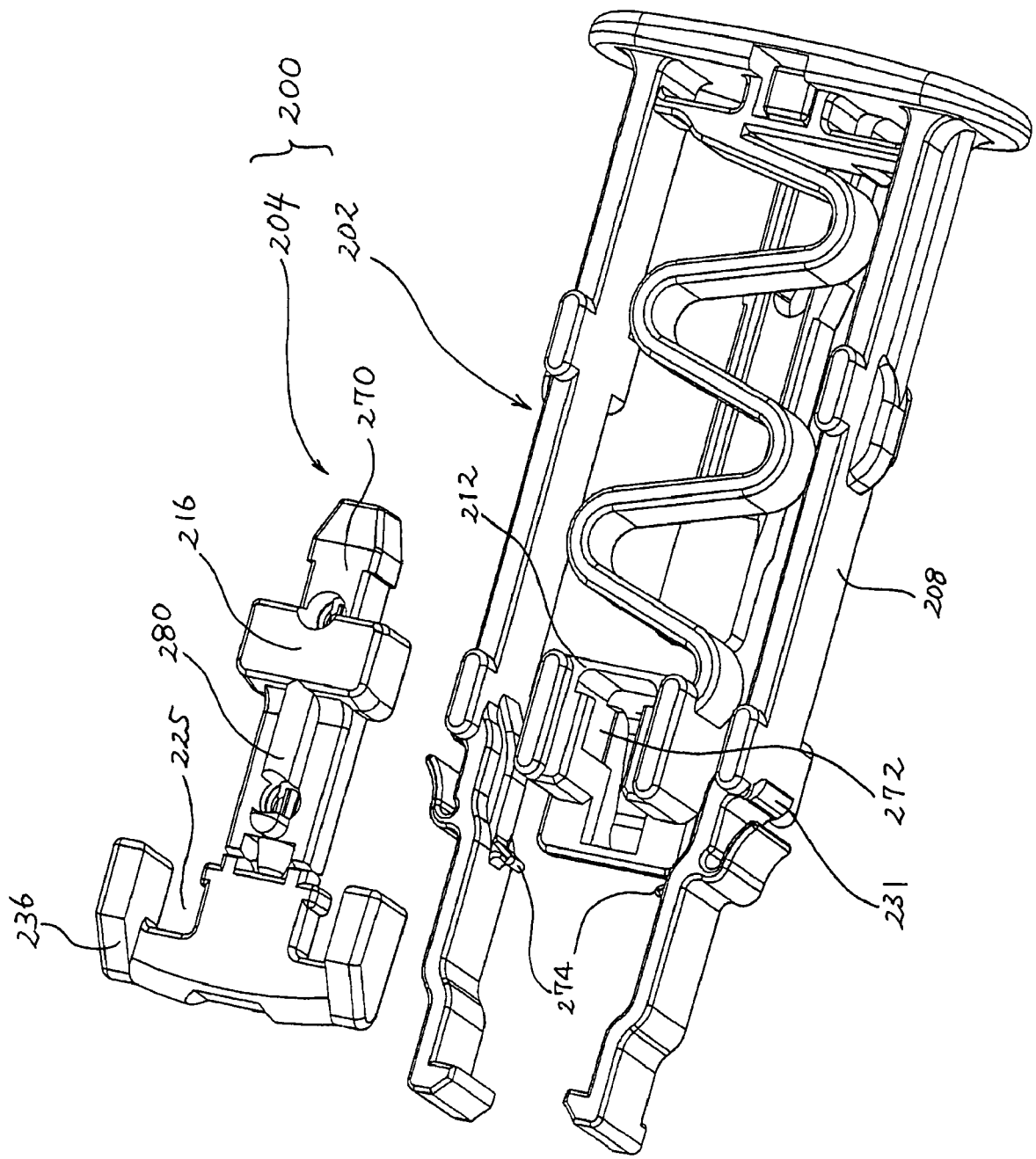
FIG. 9 is a schematic exploded view of the lancet and the ejector that constitute the lancet structure.

One example of such connection is shown in FIG. 9. In FIG. 9, the lancet body 216 as a whole has a protrusion 270, and the connector 212 has a recess 272 in which the projection can be fitted. As will be easily understood, when the protrusion 270 is moved downward and fitted in the recess 272, the connector 212 and the lancet body 216 are not separated from each other by the force acting in the front-to-back direction, so that they behave integrally. When a force acts in the vertical direction, however, the connector 212 and the lancet body 216 can be easily separated from each other. It is of advantage to employ such a connection method, since it enables it to form the lancet and the ejector separately and combine them into an integral body.

In this specification, expressions of "taper off" and "flare (or widen) forward" as to the tapered portion mean that width of the tapered portion (a dimension perpendicular to the forward direction) decreases and increases, respectively, when viewing toward the front in FIG. 1. The reverse tapered portion means that having a tapered shape which is reverse to its corresponding tapered portion. That is, when one tapers off forward and the other widens (or flares) forward, the former may be called the tapered portion and the latter called the reverse tapered portion, or the former may be called the reverse tapered portion and the latter called the tapered portion. The same are applicable also to the taper-like shape.

The pricking operation with the lancet assembly of the present invention is carried out, for example, in the following procedures:

1) First, the lancet structure 200 is inserted into the lancet holder 100 through the opening 104 positioned at the rear end (the action indicated by the arrow in FIG. 1).

2) The lancet structure 200 is moved forward in the lancet holder 100, and the front end of the protrusion 226 provided on the connector 212 or on the lancet body 216 (the protrusion is provided on the connector in the shown embodiment) is brought into contact with the rear end of the protrusion 116 serving as a stopper provided on the trigger counterpart 110 of the lancet holder 100, thereby to stop the movement of the lancet 204 and prevent it from moving further forward. That is, the lancet is restricted as to its forward movement (the state shown in FIG. 3).

3) With the lancet 204 being locked, the base 206 is pressed further forward, so as to start to compress the spring 210 its the unloaded state and thereby the spring 210 accumulates energy (the state between FIG. 3 and FIG. 4).

4) As the base 206 is pushed further into the lancet holder 100, and the arm 208 pushes the lancet cover forward, so that breakage occurs in the notch 218 (which functions as a weakened portion) between the lancet cover 214 and the lancet body 216, and the lancet cover 214 and the lancet body 216 are separated from each other (the state shown in FIG. 4). Then, as the arm 208 is moved further forward, the distal end 232 of the pricking element is exposed (the state shown in FIG. 5). It is preferable to provide a protrusion 280 on the lancet body, in order to prevent the lancet body 216 from deforming when the lancet cover 214 is separated.

5) As the base 206 is pressed into further so as to move the arm 208 further forward, the lancet cover 214 moves forward obliquely upward, and is held in contact with the inside of the front wall 234 of the lancet holder 100 (the state shown in FIG. 6).

6) As the base 206 is pressed into further so as to move forward the portion near the front end 114 of the trigger 300 as to the front of the lancet holder 100, the protrusion 116 and the protrusion 226 are released from their contact state with each other (the state shown in FIG. 6), and the spring 210 which has been compressed instantaneously expands, so as to launch the lancet body 216 and the distal end 232 of the pricking element protrudes through the opening 108 and thereby carry out the pricking (the state shown in FIG. 7).

7) Then, the spring 210 restores its original shape, and the distal end 232 of the pricking element retracts sufficiently deeply from the opening 108 (the state shown in FIG. 8).

In a preferred embodiment, as will be understood from FIG. 9, the arm 208 may have a protrusion 273 on the inside thereof. It is preferable that, when the connector 212 passes along the side of the protrusion, the protrusion is protruding from the arm toward the inside to such an extent that the connector barely touches the protrusion. When the lancet body which has retracted as shown in FIG. 8 after pricking moves forward again due to the vibration of the spring to expand and contract, and protrudes through the opening 108 again, thereby to resulting in the possibility of pricking again, and the protrusion has such a function to reduce such possibility. Although such touch occurs in the first pricking action, such touch does not substantially hamper the movement of the connector for the pricking operation since the spring 210 expands with a stronger force. However, for the connector which is urged to move forward again by the vibration after the pricking element has once retracted, the bare touch described above generates a significant resistance against the forward movement of the connector, thus making the second pricking substantially impossible.

The action of pressing the portion (for example, finger tip) from which blood sample is taken onto the opening 108 positioned at the front end of the lancet holder may be done in any stage as long as it is before the lancet body 216 is launched.

In the case of the lancet assembly of the present invention, the above procedures from 2) through 6) can be carried out continuously by pressing the base in a single stroke after disposing the lancet structure in the lancet holder. Particularly it is advantageous that the procedures from 3) through 6) can be carried out continuously. Therefore, the pressing action onto the opening may be done between the steps 1) and 2). In other embodiment, in the case wherein the assembly is delivered to the market in the state of the procedure 2), the pressing action may be done immediately before the procedure 3).

To make it easier to understand the positional relationships between the lancet structure and the lancet holder of the present invention or the positional relationships between the components which form the lancet structure and the lancet holder, FIGS. 10 to 15 show the states shown in FIGS. 3 to 8, respectively, in schematic sectional views along the central line of the lancet holder (the line X-X in FIG. 3).

Figure 10:
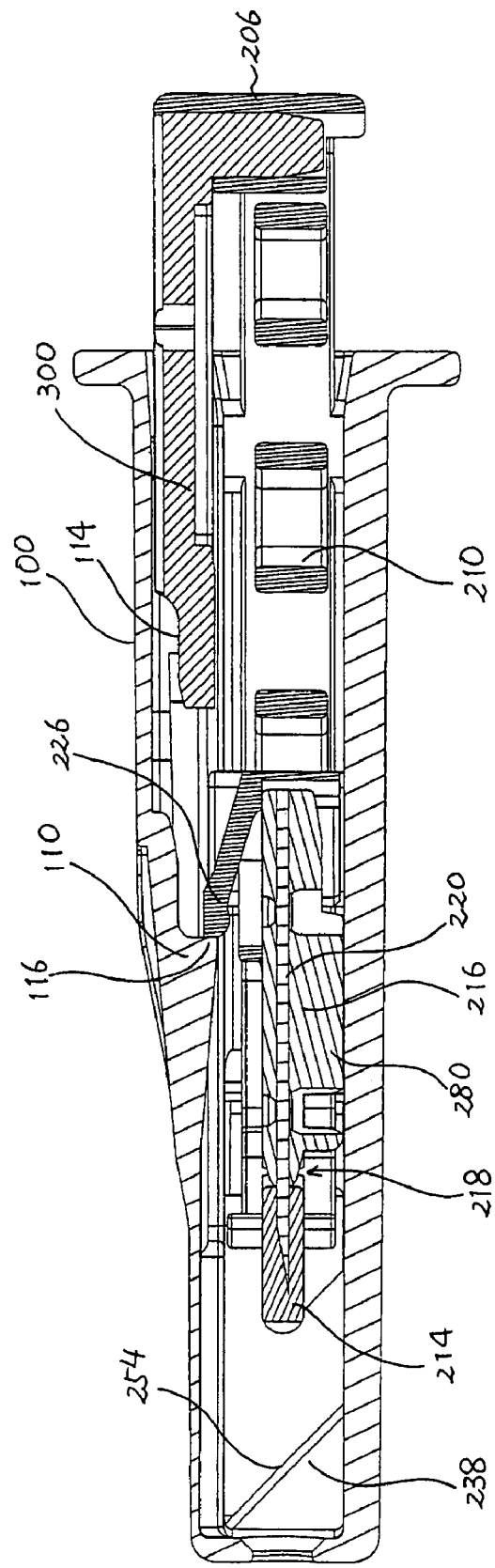
FIG. 10 is a schematic sectional view along line X-X in FIG. 3.

FIG. 10 is a sectional view corresponding to the state shown in FIG. 3. In FIG. 10, it is seen that the protrusion 226 of the connector 212 abuts against the protrusion 116 positioned at a lower and rear position of the trigger counterpart 110 of the lancet holder 100. The V-shaped notch 218 integrally connects the lancet cover 214 and the lancet body 216.

Figure 11:
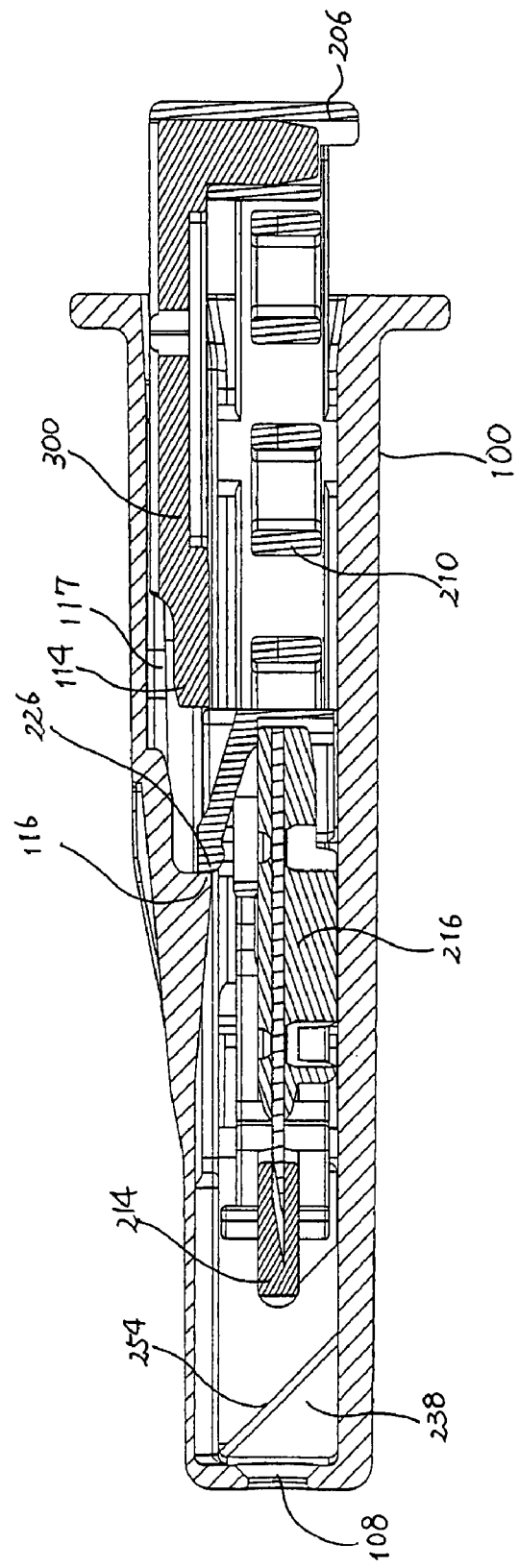
FIG. 11 is a schematic sectional view of the state shown in FIG. 4, similarly to FIG. 9.

FIG. 11 is a sectional view corresponding to the state shown in FIG. 4. In FIG. 11, the lancet cover 214 is separated from the lancet body 216. It can also be seen that the spring 210 is compressed in comparison to the state shown in FIG. 10.

Figure 12:
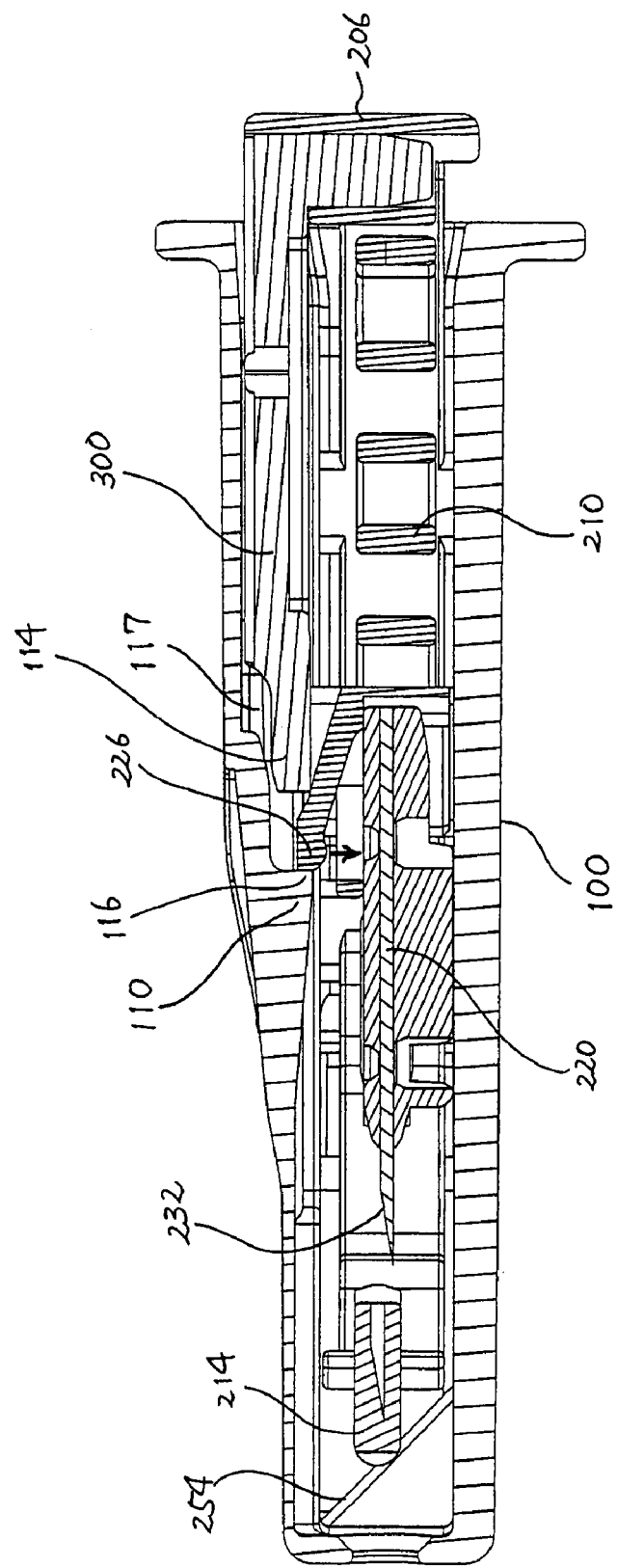
FIG. 12 is a schematic sectional view of the state shown in FIG. 5, similarly to FIG. 9.

FIG. 12 is a sectional view corresponding to the state shown in FIG. 5. In FIG. 12, the lancet cover 214 is removed from the pricking element 220 so as to expose the distal end thereof.

As will be understood from FIG. 12, the front end 114 of the trigger 300 has just been in contact with the protrusion 226 (specifically the inclined surface thereof) which protrudes forward obliquely upward from the connector 212 that is in contact with the protrusion 116 positioned at the lower back of the trigger counterpart 110. Therefore, when the base is pressed further from this state, the front end 114 gradually presses the protrusion 226 downward while the arms move forward so that the lancet cover moves up the inclined surface and eventually achieves the state shown in FIG. 13.

Figure 13:
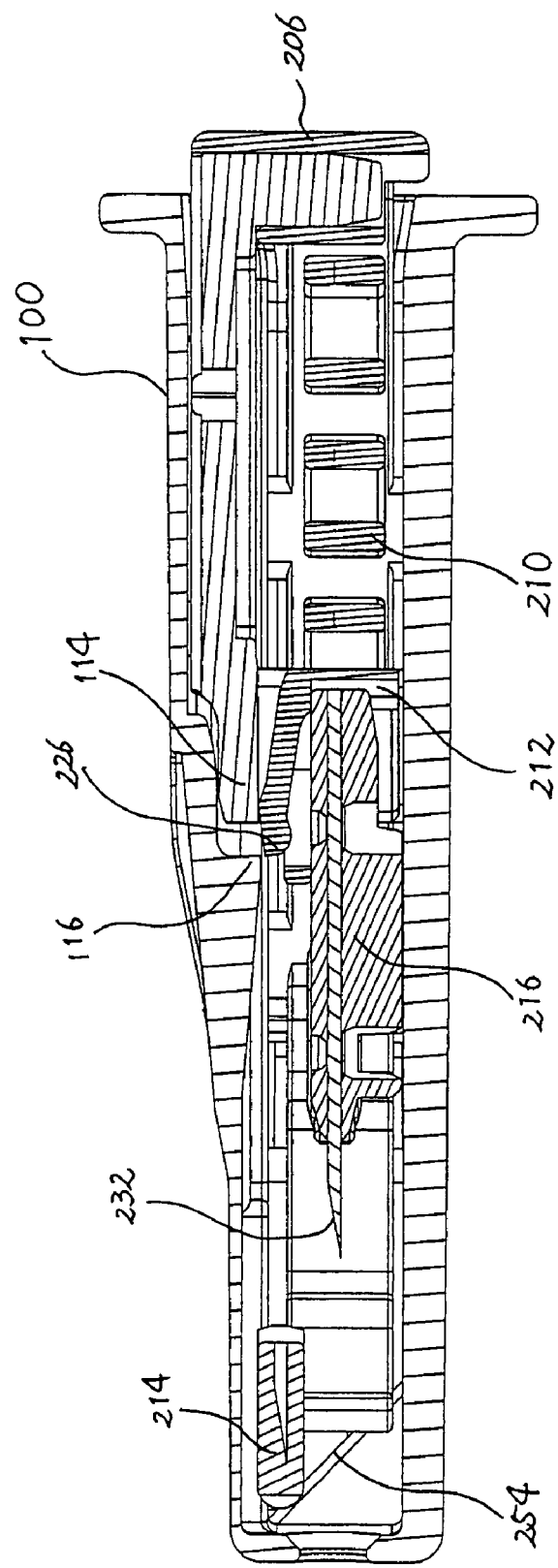
FIG. 13 is a schematic sectional view of the state shown in FIG. 6, similarly to FIG. 9.

FIG. 13 is a sectional view corresponding to the state shown in FIG. 6. In FIG. 13, the lancet cover 214 is in contact with the inside of the front wall 234 of the lancet holder. As will be seen from the drawing, the lancet cover 214 moves upward in addition to moving forward, in contrast to the state shown in FIG. 12, in other words, the lancet cover moves forward and obliquely upward. This is because the tapered portions 236 positioned on the lateral faces of the lancet cover move along the inclined surface 254 of the tapered portions 238 provided on the inside of the front wall of the lancet holder. This state is immediately after the front end 114 of the trigger has moved forward while pressing the protrusion 226 further downward (refer to the arrow in FIG. 12), and the protrusion 226 protruding forward obliquely upward from the connector 212 has just been released from the contact with the protrusion 116 which is positioned at the lower back of the trigger counterpart 110, from which state the operation proceeds to the state shown in FIG. 7.

Figure 14:
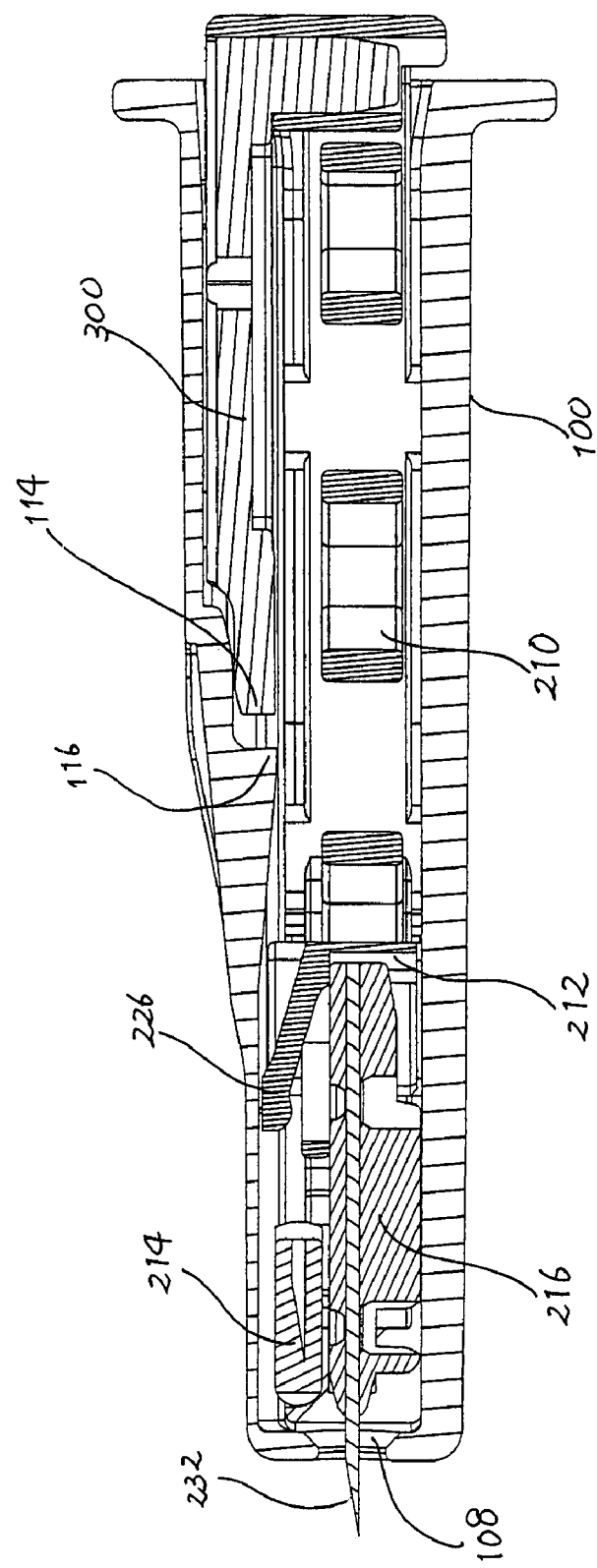
FIG. 14 is a schematic sectional view of the state shown in FIG. 7, similarly to FIG. 9.

FIG. 14 is a sectional view corresponding to the state shown in FIG. 7. In FIG. 14, the distal end 232 of the pricking element is protruding from the opening 108 positioned at the front end of the lancet holder 100. As will be seen from the drawing, the lancet cover 214 has just moved forward and obliquely upward, and therefore does not hamper the movement of the pricking element at all.

Figure 15:
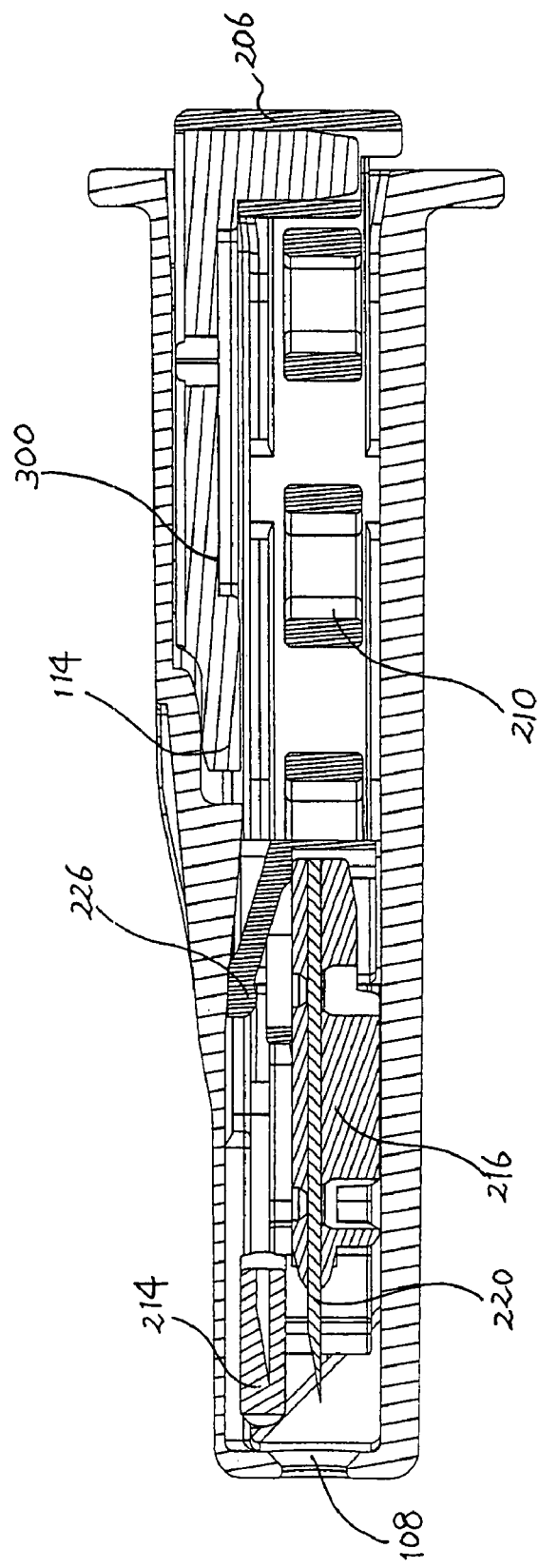
FIG. 15 is a schematic sectional view of the state shown in FIG. 8, similarly to FIG. 9.

FIG. 15 is a sectional view corresponding to the state shown in FIG. 8. In FIG. 15, the distal end 232 of the pricking element is retracted by a distance sufficiently long from the opening 108 positioned at the front end of the lancet holder 100. As will be seen from the drawing, it is quite difficult to touch the distal end 232 of the pricking element through the opening 108, and such touching is substantially impossible unless it is deliberately attempted.

The lancet assembly of the present invention has been described with reference to the accompanying drawings. However, the sectional shape of the lancet assembly perpendicular to the pricking direction needs not to be a little elongated rectangle or polygon as shown, and may be an ellipse, an oval, a circle, a polygon or any other shape as required. For example, in the embodiment shown in the drawing, the above mentioned cross section may be proximate to a circle with the spring being turned 90 degrees around the pricking direction and connected to the connector and the base.

The lancet assembly of the present invention as described above provides means for more readily taking a blood sample.

The invention claimed is:

1. A lancet assembly comprising:
   a lancet structure including an ejector and a lancet, the ejector comprising a trigger, an arm, a spring having a front end and a rear end, and a base attached to the trigger, the arm, and the spring, the spring having a connector provided on the front end, and being connected to the base at the rear end, and the lancet comprising a lancet body connected to the connector, a lancet cover, and a pricking element having a distal end, the pricking element being disposed within and straddling across the lancet body and the lancet cover, and the distal end of the pricking element being enclosed by the lancet cover, the lancet cover including a tapered portion; and
   a lancet holder having reverse tapered portion, a front end and an opening configured to enable the distal end of the pricking element to pass therethrough, the lancet holder being configured to hold the lancet structure,
   wherein when the lancet structure is inserted into the lancet holder and the base is moved toward the connector so as to compress the spring with the connector being engaged with the lancet holder, the lancet cover is separated from the pricking element by movement in an oblique direction of the lancet cover by the tapered portion of the lancet cover being moved along the reverse tapered portion of the lancet holder, relative to the pricking element, which remains substantially in the same position, thereby exposing the distal end of the pricking element which has been enclosed, and when the base is further moved thereafter, the trigger disengages the engaged connector.

2. The lancet assembly according to claim 1 wherein the lancet cover is configured to be automatically separated from the pricking element.

3. The lancet assembly according to claim 1 wherein the pricking element is disposed in the lancet cover, and the lancet cover is arranged so as to be displaced laterally relative to a longitudinal direction of the pricking element when the spring is compressed so as to enable the pricking element to pass through the opening in the lancet holder.

4. The lancet assembly according to claim 1 wherein the lancet cover and the lancet body are integrally connected by a weakened portion which is located therebetween.

5. The lancet assembly according to claim 1 wherein the lancet cover and the lancet body are separate members.

6. The lancet assembly according to claim 4 wherein
the arm includes a front end;
the lancet cover includes a rear side and is located in front of the arm; and
when the base is moved toward the connector so as to compress the spring while keeping the front end of the arm in contact with the rear side of the lancet cover, the lancet cover is separated from the lancet body at the weakened portion.

7. The lancet assembly according to claim 5 wherein
the arm includes a front end;
the lancet cover includes a rear side and is positioned in front of the arm;
when the base is moved toward the connector so as to compress the spring while keeping the front end of the arm in contact with the rear side of the lancet cover, the lancet cover moves forward relative to the lancet body.

8. The lancet assembly according to claim 1 wherein a front end of the arm engages the lancet cover.

9. The lancet assembly according to claim 8 wherein the front end of the arm comprises a hooked portion or an L-shaped portion which is bent inward, and the lancet cover comprises on a side a portion which engages said hooked portion.

10. The lancet assembly according to claim 1 wherein the separated lancet cover is moved forward and obliquely by the arm when the arm is moved forward, so that the opening at the front end of the lancet holder is located in front of the exposed distal end of the pricking element.

11. The lancet assembly according to claim 10 wherein
the lancet holder has a guide provided on a side inner wall at the front end thereof;
the lancet cover has a guided device which is guided by the guide; and
the guide and the guided device cooperate so that the lancet cover which has been separated is moved forward by the arm moving forward while the lancet cover moves forward and obliquely upward.

12. The lancet assembly according to claim 1 wherein the base, the arm, the spring and the connector of the base are integrally formed of a resin.

13. The lancet assembly according to claim 1 wherein the lancet body and the lancet cover are formed by molding a resin integrally with the pricking element.

14. The lancet assembly according claim 4 wherein the weakened portion comprises a notch portion, and the lancet cover is separated from the lancet body and from the pricking element through breakage of the notch portion.

15. The lancet assembly according to claim 1 wherein the connection of the lancet body to the connector is achieved by the lancet body and the connector both comprising complementary forms which are able to engage each other and which are unable to be separated in a pricking direction.

16. The lancet assembly according to claim 15 wherein the connector comprises a recess and the lancet body comprises a protrusion which is engaged with the recess.

17. The lancet assembly according to claim 1 wherein the lancet body and the connector are originally formed integrally.

18. The lancet assembly according to claim 1 wherein the connector comprises a protrusion,
when the spring is compressed, the protrusion of the connector abuts against a protrusion of the lancet holder so that forward movement of the connector is prevented, forming an abutment state, and
the trigger releases the abutment state.

19. The lancet assembly according to claim 1 wherein the spring comprises a protrusion,
when the spring is compressed, the protrusion of the spring abuts against a protrusion of the lancet holder so that forward movement of the connector is prevented, forming an abutment state, and
the trigger releases the abutment state.

20. The lancet assembly according to claim 1 wherein the lancet body comprises a protrusion,
when the spring is compressed, the protrusion of the lancet body abuts against a protrusion of the lancet holder so that forward movement of the connector is prevented, forming an abutment state, and
the trigger releases the abutment state.

21. The lancet assembly according to claim 1 wherein the arm comprises a guide pin, and
the lancet holder comprises a channel on an inner wall which guides said guide pin.

22. The lancet assembly according to claim 1 wherein the connector comprises a guide pin, and
the lancet holder comprises a channel on an inner wall which guides said guide pin.

23. The lancet assembly according to claim 1 wherein the base comprises a pair of the arms, and the spring is located between the arms.

24. The lancet assembly according to claim 19 wherein the connector, the lancet body or the spring comprises a protrusion which extends in a forward and oblique direction therefrom, and
when the trigger which moves forward with respect to the forward and oblique direction comes into contact with said protrusion and pushes said protrusion forward, the connector, the lancet body or the spring is pushed downward and the abutment state is released.

25. The lancet assembly according to claim 1 wherein a rear end of the spring is connected to a foot of the arm where the arm is attached to the base or to a vicinity of the foot in addition to or in place of to being connected to the base.

26. The lancet assembly according to claim 1 wherein a rear end of the trigger is connected to a foot of the arm where the arm is attached to the base or to a vicinity of the foot in addition to or in place of to being connected to the base.

* * * * *